United States Patent
Garcia et al.

(10) Patent No.: US 10,352,933 B2
(45) Date of Patent: Jul. 16, 2019

(54) VISUALIZATION OF BACTERIAL COLONIZATION AND BIOFILM FORMATION ON ORTHOPAEDIC TRAUMA EXPLANTS

(71) Applicant: RHODE ISLAND HOSPITAL, Providence, RI (US)

(72) Inventors: Dioscaris Garcia, Pawtucket, RI (US); Christopher T. Born, Philadelphia, PA (US); John Jarrell, East Greenwich, RI (US)

(73) Assignee: Rhode Island Hospital, Providence, RI (US)

( * ) Notice: Subject to any disclaimer, the term of this patent is extended or adjusted under 35 U.S.C. 154(b) by 301 days.

(21) Appl. No.: 14/899,972

(22) PCT Filed: Dec. 17, 2015

(86) PCT No.: PCT/US2015/066460
§ 371 (c)(1),
(2) Date: Dec. 18, 2015

(87) PCT Pub. No.: WO2016/100712
PCT Pub. Date: Jun. 23, 2016

(65) Prior Publication Data
US 2016/0370367 A1 Dec. 22, 2016

Related U.S. Application Data

(60) Provisional application No. 62/094,004, filed on Dec. 18, 2014.

(51) Int. Cl.
| | | |
|---|---|---|
| G01N 33/50 | (2006.01) | |
| G01N 33/569 | (2006.01) | |
| G02B 21/16 | (2006.01) | |
| G02B 21/36 | (2006.01) | |
| G01N 21/64 | (2006.01) | |
| G02B 21/00 | (2006.01) | |

(52) U.S. Cl.
CPC ... *G01N 33/56911* (2013.01); *G01N 21/6428* (2013.01); *G01N 21/6458* (2013.01); *G02B 21/0028* (2013.01); *G02B 21/0056* (2013.01); *G02B 21/0076* (2013.01); *G02B 21/16* (2013.01); *G02B 21/365* (2013.01); *G01N 2021/6439* (2013.01); *G01N 2333/195* (2013.01); *G01N 2333/22* (2013.01); *G01N 2333/31* (2013.01)

(58) Field of Classification Search
None
See application file for complete search history.

(56) References Cited

U.S. PATENT DOCUMENTS

| | | | |
|---|---|---|---|
| 8,323,903 B2 | 12/2012 | Archer et al. | |
| 9,089,677 B2 | 7/2015 | Soo et al. | |
| 2002/0054429 A1 | 5/2002 | Engelhardt et al. | |
| 2005/0214279 A1 | 9/2005 | Silverstein et al. | |
| 2007/0269902 A1 | 11/2007 | Beechem et al. | |
| 2011/0117025 A1 | 5/2011 | Dacosta et al. | |
| 2011/0236306 A1* | 9/2011 | Goodman | A61K 38/164 424/1.49 |
| 2011/0305717 A1 | 12/2011 | Gorvell et al. | |
| 2012/0220981 A1 | 8/2012 | Soo et al. | |
| 2013/0064762 A1 | 3/2013 | Simon | |
| 2016/0311877 A1* | 10/2016 | Watters | G01N 33/569 |

FOREIGN PATENT DOCUMENTS

| | | |
|---|---|---|
| CA | 2724973 C | 8/2015 |
| DE | 10055176 B4 | 5/2007 |
| WO | 1997035614 A1 | 10/1997 |

OTHER PUBLICATIONS

Broekhulzen et al., Tissue around catheters is a niche for bacteria associated with medical device infection, Crit Care Med 2008, vol. 36, No. 8, pp. 2395-2402. (Year: 2008).*
Becerra et al., An optimized staining technique for the detection of Gram positive and Gram negative bacteria within tissue, BMC Res Notes, 2016, 9: 216, pp. 1-10 (Year: 2016).*
Broekhuizen et al., Microscopic detection of viable *Staphylococcus epidermidis* in Peri-Implant Tissue in Experimental Biomaterial-Associated Infection, Identified by Bromodeoxyuridine Incorporation, Infection and Immun8ity, Mar. 2010, pp. 954-962. (Year: 2010).*
Hassan et al., Evaluation of different detection methods of biofilm formation in the clinical isolates, Braz J. Infect Dis 2011, 15(4), pp. 305-311. (Year: 2011).*
Broekhulzen et al., Tissue around catheters is a niche for bacteria associated with medical device infection, Crit Care Med 2008, vol. 36, No. 8, pp. 2395-2402. (2008).
Becerra et al., An optimized staining technique for the detection of Gram positive and Gram negative bacteria within tissue, BMC Res Notes, 2016, 9: 216, pp. 1-10 (2016).
Broekhuizen et al., Microscopic detection of viable *Staphylococcus epidermidis* in Peri-Implant Tissue in Experimental Biomaterial-Associated Infection, Identified by Bromodeoxyuridine Incorporation, Infection and Immun8ity, Mar. 2010, pages 954-962. (2010).
Hassan et al., Evaluation of different detection methods of biofilm formation in the clinical isolates, Braz J. Infect Dis 2011, 15(4), pp. 305-311. (2011).
Extended European Search Report received in European Application No. 15871100.2, dated Nov. 28, 2018, 7 pages.

(Continued)

*Primary Examiner* — Gary Counts
(74) *Attorney, Agent, or Firm* — Adler, Pollock & Sheehan P.C.

(57) ABSTRACT

Detection and quantification of microbial colonization and biofilm formation on orthopedic explants would be important for deciding treatment interventions at the time of surgery. Methods and Systems for such treatments are shown that utilize various steps and kits to quickly generate confocal laser-scanning microscopy (CLSM) images to allow for the detection and quantification. The explants are prepared by applying antibodies of both gram-positive and grain-negative for at least one period of time.

9 Claims, 31 Drawing Sheets

(56) References Cited

OTHER PUBLICATIONS

Gorman et al., "Confocal Laser Scanning Microscopy of Peritoneal Catheter Surfaces", Journal of Medical Microbiology, Jun. 1, 1993, vol. 38, pp. 411-417.
International Search Report and Written opinion received in International Application No. PCT/US2015/066460, dated Feb. 26, 2016, 10 pages.
Zijinge et al., "Oral Biofilm Architecture on Natural Teeth," PLoS One, Feb. 24, 2010, vol. 5, Issue 2, e9321, pp. 1-9.

\* cited by examiner

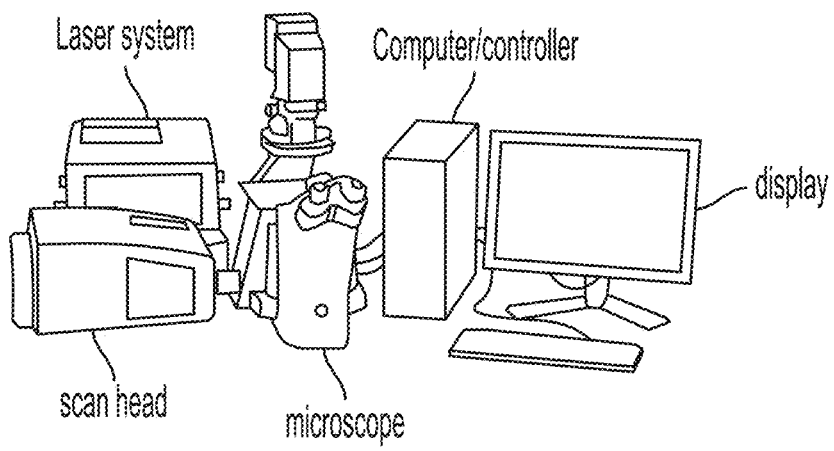
Figure 5
Figure 6
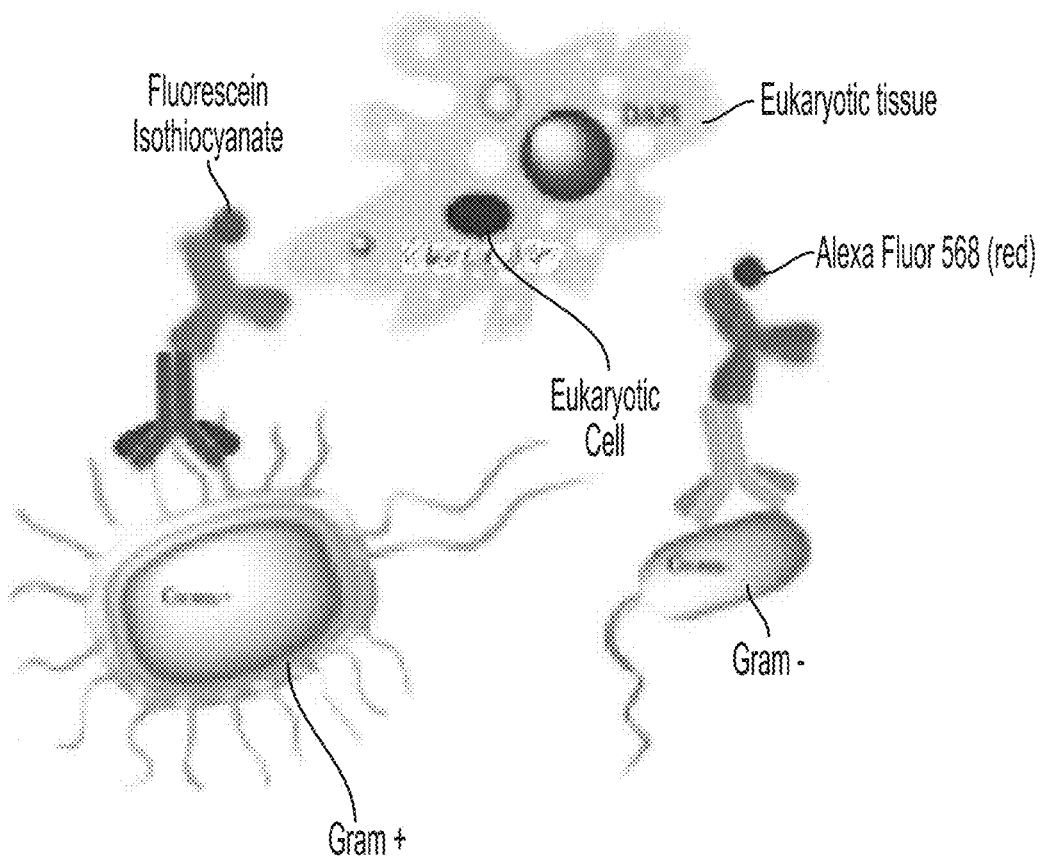

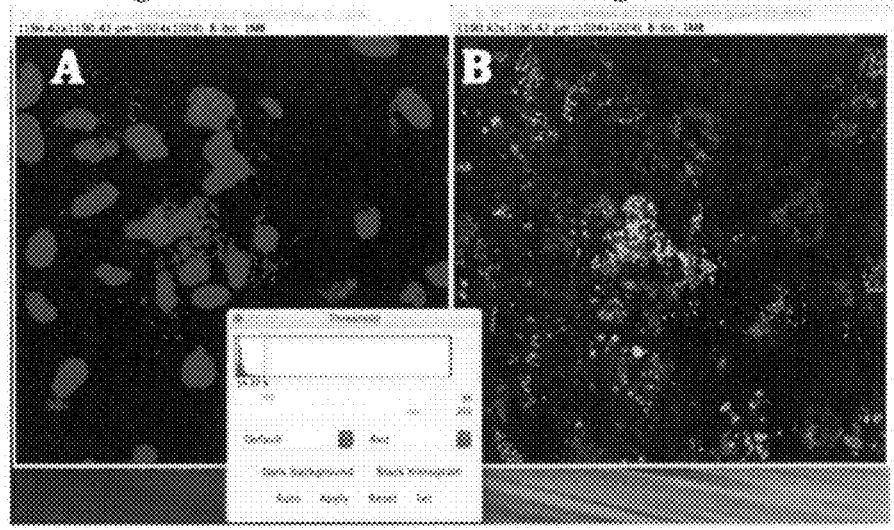

VISUALIZATION OF BACTERIAL COLONIZATION AND BIOFILM FORMATION ON ORTHOPAEDIC TRAUMA EXPLANTS

CROSS-REFERENCE TO RELATED APPLICATION

This application claims priority to International Application No. PCT/US2015/0660460 filed Dec. 17, 2015, which claims priority to U.S. Provisional Patent Application No. 62/094,004, filed Dec. 18, 2014, which is incorporated herein by reference.

BACKGROUND OF THE INVENTION

1. Field of the Invention

The subject disclosure relates to systems and methods for rapid quantification and characterization of microbial colonization and biofilm formation on implants at the time of removal.

2. Background of the Related Art

Microbial infection and biofilm formation on orthopaedic trauma implants is one of the most serious problems in orthopaedic surgery. The formation of biofilms increases resistance to antibiotic treatment, and typically an orthopaedic device that becomes infected must be removed. In many cases, the heterogeneity of the tissue surrounding the complex surface of the implant may complicate the identification of microbial colonization or infection. Subsequent analysis to determine the bacterial colonization, adhesion, and species on the explant may take several days or weeks, negatively impacting the efficacy and efficiency of possible treatment plans. In many cases, current detection methods may yield false-negative findings, which further exacerbate the problem.

Based on projections from 2004, of an estimated two million fracture-fixation devices implanted annually in the U.S. the number of infected implants was greater than 100,000 cases, or 5% overall. The field of orthopaedic trauma encounters significantly higher rates of infection. With open fractures (fractures in which the bone has violated the skin and soft tissue) incidence of infection may exceed 30%. The overall infection rate of trauma patients is extremely high, with specific incidence depending on fracture type.

Furthermore, this infection rate dramatically increases in traumatic extremity injuries sustained during combat and in developing countries. Despite many strategies in infection treatment, including prophylactic antibiotic administration, surgical debridement and irrigation, and post-surgical antibiotic regimens, an orthopaedic device that becomes infected typically must be removed, or 'explanted'.

These one- or two-step revision surgeries mean delayed healing time, increased medical costs, and less successful post-operative outcomes. One of the greatest ongoing challenges in the field of orthopaedic trauma remains decreasing the rates and consequent ill effects of bacterial infection.

One of the principal factors challenging effective infection treatment is the formation of bacterial biofilm, a coating of bacterial film that adheres to the infected tissue and/or orthopaedic implant. Biofilm formation proceeds as a four-step process: 1) initial attachment of bacterial cells; 2) cell aggregation and accumulation in multiple cell layers; 3) biofilm maturation and 4) detachment of cells from the biofilm into a planktonic (drifting) state to initiate a new cycle of biofilm formation elsewhere. Complexes of tightly attached bacterial communities follow, which display cell-to-cell signaling and exist within a strong extracellular polymer matrix.

Biofilms make bacteria more resistant to antibiotic treatment and enable them to cause recurrent infection. Biofilms are difficult to eradicate because most antibiotics are unable to penetrate their surface, weakening the primary line of attack. Additionally, biofilms make the enclosed bacteria resistant to many effects of the host's immune system. To combat biofilm-centered implant infections, new treatment strategies are being developed, including anti-infective or infective-resistant implant materials. Through modifying the biomaterial surface to give anti-adhesive properties, doping the material with antimicrobial substances, combining anti-adhesive and antimicrobial effects, or designing materials to oppose biofilm formation and support bone repair, biofilm formation can be markedly decreased.

Despite advances in infection treatment, one of the most comprehensive problems in fracture management and treatment is the need for rapid and accurate identification and quantification of microbial contamination or infection. There are several available clinical options for infection diagnosis, including the standard bacterial isolation and culture, and molecular processing techniques. In the standard isolation and culture method, swabs from multiple sites are taken from the affected area, cultured on plates in the laboratory, and isolated. However, a limited amount of bacteria swabbed or biofilm-adhered bacteria can decrease the probability of detection, yielding false-negative findings.

Because the bacterial swabs are grown and cultured in the laboratory, contamination from multiple sources during processing (e.g., surgeon, technician, other samples, laboratory environment) is possible. Importantly, analysis to determine the presence of bacterial colonization, adhesion, and species on the explant may take several days, contingent on the length of time the bacterial species requires to grow. This time lag between treatment and diagnosis, in addition to potentially faulty findings, negatively impacts the efficacy of current treatment plans.

Another diagnostic test less commonly employed is 16S rRNA molecular testing, which identifies pathogens based on analyzing and sequencing the bacterial 16S molecular marker. While this technique was found to have a high level of identification accuracy and specificity, these tests are not widely available, and identification of species requires bacterial sequencing and species-specific primers. Furthermore, molecular probes do not provide susceptibility testing, which predicts in vivo success or failure of a directed antibiotic therapy. Genomic probes—such as real-time PCR—are dependent on isolation, prone to contamination, and have a turnaround time of several hours to days. Additionally, these tests have been found to be more expensive than traditional bacterial culture and isolation techniques.

SUMMARY

When any implant is removed during the process of any revision surgery it is important to know if there is an infection present. The development of a clinically-relevant rapid assay (visual or chemical or otherwise) for the detection and quantification of microbial colonization and biofilm formation on orthopaedic explants would be important for deciding treatment interventions at the time of surgery. Currently there is no reliable, rapid diagnostic tool that allows for real-time detection of bacterial presence.

For example, counting the number of cells per high-power field is notoriously unreliable and polymerase chain reaction studies (PCR) still take many hours to complete. Laboratory cultures may take days or weeks to yield a result and still may not be accurate if there is contamination.

Therefore, there remains a need in the prior art for a reliable, rapid diagnostic tool that allows for real-time detection of bacterial presence on potentially infected explants, tissue surfaces, bone cements etc. Preferably, the systems and methods would take advantage of existing equipment and materials that are already typically present or available in the hospital setting. The systems and methods also can and accurately detect and characterize bacterial biofilm formation on potentially infected explant and tissue surfaces.

The subject technology revolves around the visualization, characterization, and quantification of bacterial biofilms formed on the surfaces of explanted hardware from orthopaedic trauma patients with known infections. By employing the techniques of fluorescent conjugated bacteria antibodies (FCBA) and confocal laser-scanning microscopy (CLSM), the subject technology provides a faster, visual means for identifying bacterial presence on the surface of orthopaedic hardware at the time of removal.

Fluorescent conjugated bacteria antibodies rely on the physiological tenets of the immune system to identify varying types of cells. Antibodies harvested and purified from a host's immune system (specific to a particular pathogen) attach to their pathogen when introduced to a given sample, just as they would in the host's body. These primary antibodies are labeled with a "secondary" antibody, which is conjugated to a fluorescent dye. The coupling of the secondary "fluorochrome" to the primary antibody forms the basis of immunofluorescent staining. Once the secondary antibody (specific to a particular primary) attaches to the primary adhered to a specific pathogen, that sample can then be imaged and analyzed with CLSM.

A confocal laser-scanning microscope consists of a standard microscope in concert with a dark-field condenser and an ultraviolet light source. The continuous UV lasers provide different wavelengths of light to the sample stage, which align with the absorbance wavelengths of the various secondary fluorochrome antibodies used. This specificity enables differential identification of multiple species types on a single sample (via different wavelengths of secondary fluorescence and subsequent identification. Another advantage of CLSM is the ability to image a sample three-dimensionally, as opposed to the traditional 2D image capture of a typical microscope. The confocal microscope is able to take "z" slices imaging in the depth direction of the sample. This allows for a composite three-dimensional rendering of the entire explant or sample, which provides valuable information on the location, complexity, coverage, and composition of the present bacterial biofilm.

The subject technology uses the ability of FCBA and CLSM to effectively and accurately label and identify bacterial species. The Gram Stain test is a fundamental method to differentiate between bacterial types, and forms the basis of differential bacterial identification in FCBA assays. To prove the concept, *Staphylococcus aureus* was utilized as our Gram-positive bacteria and *Acinetobacter baumannii* was our Gram-negative bacteria studied. These bacteria were respectively inoculated at a standardized concentration into glass-bottom well plates, cultured, and fixed according to protocols in accordance with the subject technology. The bacteria is then respectively labeled with Gram-positive or Gram-negative FCBA's and analyzed with CLSM.

Co-cultures of both Gram-positive and Gram-negative bacteria can also be done in the same well plates. The subject technology uses Gram-positive and Gram-negative antibodies to ensure that the Gram-negative FCBA labeled only gram-negative species and the Gram-positive FCBA labeled only gram-positive species. Methods and systems in accordance with the subject technology can simultaneously differentiate between Gram positive and Gram-negative species in the same sample, which can be a wide variety of explant types. The subject technology can quantify bacterial biofilm on explants and tissue, thereby helping to inform a surgeon's intervention and treatment regimen both during and after surgery.

One embodiment is directed to a method for visualizing and quantifying bacterial colonization and biofilm formation on an explant comprising the steps of washing the explant at least once with a first solution of PBS Blocking Buffer and 1% Rabbit Serum (RS) straight through; applying conjugated antibodies of both gram-positive and gram-negative for a first period of time; washing the explant at least once with PBS Blocking Buffer and 1% RS straight through; introducing 2° antibody of both gram-positive and gram-negative for a second period of time; rinsing with PBS Blocking Buffer and 1% RS; and viewing the explants with confocal laser scanning microscopy (CLSM) for gram-positive and gram-negative adherence. The method may be such the at least once wash of steps 1) and 3) is three times each; and the first and second periods of time are approximately 15 minutes each.

The explants may be wrapped in tin foil throughout one or more of the steps to prevent light-induced damage and photobleaching. Multiple iterations of antibody dilution testing in bacterial plates can be performed to ensure balanced fluorescence between antibody types of gram positive and gram negative primary and secondary to minimize bleedthrough. A rocker may hold the explant in a kit for a gentle washing effect such as at 30 rpm. The images from the CLSM can also be arranged into a three-dimensional rendering of a surface of the explants.

Another embodiment of the subject technology is directed to method for visualizing and quantifying bacterial colonization and biofilm formation on explants. The method includes washing the explant at least once with a first solution of PBS Blocking Buffer and 1% Rabbit Serum (RS) straight through and blocking with a second solution of 50% Bovine Serum Albumin (BSA) and 50% RS for a first period of time. A 1° antibody of both gram-positive and gram-negative is introduced for a second period of time. Then, the explants is washed at least once with PBS Blocking Buffer and 1% RS straight through. A 2° antibody of both gram-positive and gram-negative is introduced for a third period of time followed by rinsing with PBS Blocking Buffer and 1% RS. Once so prepared, the explants can be viewed with confocal laser scanning microscopy for gram-positive and gram-negative adherence. This method can be such that the at least once wash of steps is three times each and the first, second and third periods of time are approximately 15 minutes each.

It should be appreciated that the subject technology can be implemented and utilized in numerous ways, including without limitation as a process, an apparatus, a system, a device, a method for applications now known and later developed or a computer readable medium. These and other unique features of the system disclosed herein will become more readily apparent from the following description and the accompanying drawings.

BRIEF DESCRIPTION OF THE DRAWINGS

So that those having ordinary skill in the art to which the disclosed system appertains will more readily understand how to make and use the same, reference may be had to the following drawings.

FIG. 5 is a system for confocal laser scanning microscopy (CLSM).

FIG. 6 is an exemplary grain positive fluorescein isothiocyanate (FITC) showing green (Ex 492 nm-EM 518 nm) and gram negative Alexa Fluor shows red (Ex 578 nm-EM 603 nm) in accordance with the subject disclosure.

FIG. 7A is a threshold saturation determinations of observed eukaryotic staining in accordance with the subject disclosure.

FIG. 7B is grayscale of the green channel with visible cocci of FIG. 7A in accordance with the subject disclosure.

In FIG. 31, the primary antibody binds to the antigen recognition site, which is located on the bacteria (i.e., LTA or LPS). The conjugated secondary antibody is conjugated to the fluorophore. The antibodies are capable of penetrating biofilm, which is evident by the fact that the bacteria in biofilm fluoresces and is visible on an orthopaedic explants under CLSM.

DETAILED DESCRIPTION OF PREFERRED EMBODIMENTS

Figure 1A:
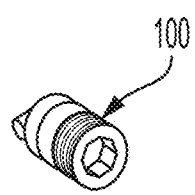
FIG. 1A is an image of a screw explant.

The subject technology overcomes many of the prior art problems associated with quantifying and characterizing microbial colonization and biofilm formation on explants. The advantages, and other features of the system disclosed herein, will become more readily apparent to those having ordinary skill in the art from the following detailed description of certain preferred embodiments taken in conjunction with the drawings which set forth representative embodiments of the present invention and wherein like reference numerals identify similar structural elements. It is understood that references to the figures such as up, down, upward, downward, left, and right are with respect to the figures and not meant in a limiting sense.

Figure 1B:
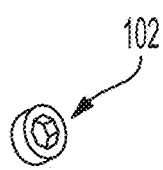
FIG. 1B is an image of a screw head explant.
Figure 1C:
FIG. 1C is an image of a bone cement explant.
Figure 2A:
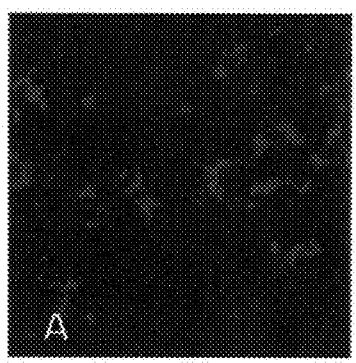
FIG. 2A is a confocal microscopy image of the explant of FIG. 1A in accordance with the subject disclosure.
Figure 2B:
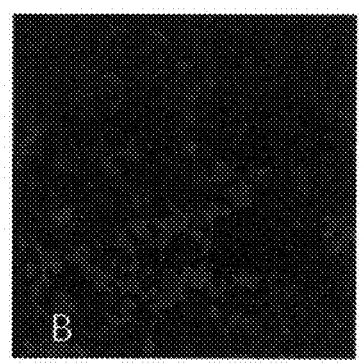
FIG. 2B is a confocal microscopy image of the explant of FIG. 2B in accordance with the subject disclosure.
Figure 2:
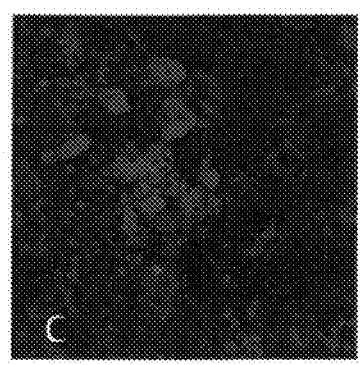
FIG. 2C is a confocal microscopy image of the explant of FIG. 2C in accordance with the subject disclosure.

Referring now to FIGS. 1A-C, typical explants are shown. FIG. 1A is a top portion of a screw 100. FIG. 1B is a screwhead 102. FIG. 1C is a polymethyl methacrylate bone cement fragment 104. Referring now to FIGS. 2A-C, each is a confocal laser scanning micrograph taken of the explants of FIGS. A-C, respectively, after application of a methodology herein. FIGS. 2A-C are labeled with DAPI (blue) for eukaryotic cell labeling, FITC-conjugated gram-positive antibody (green), and Alexa Fluor-conjugated gram-negative antibody displaying heavy bacterial colonization.

Several methods for preparing explants for confocal laser scanning microscopy (CLSM) are described below. One method uses fluorescent-conjugated antibodies (FCBA). The explants are labeled with gram positive and gram negative antibodies, conjugated to fluorescein Isothiocyanate (FITC) (available from Thermo Scientific of Rockford, Ill.) and Alexa Fluor 568 (available from Life Technologies of Grand Island N.Y.). 4',6' diamidino-2-phenylindole (DAPI) was used to identify eukaryotic tissue (available from Thermo Scientific of Rockford, Ill.). A gram-negative bacterial species (e.g., Multi-drug Resistant *Acinetobacter baumannii*), and a gram-positive species (e.g., Methicillin-Sensitive *staphylococcus aureus*) were cultured in glass-bottom well plates, fixed, and labeled for confocal analysis as positive controls to establish antibody dilutions and lot quality. Through repeated trials, the protocol was further optimized for time efficiency and clear visualization and characterization of each individual sample type (e.g., screws, plates, and polymethyl methacrylate fragments). Bacterial quantification was determined based on review of the results of the CLSM.

As can be seen, a clinically-relevant rapid detection assay capable of visualizing and quantifying bacterial colonization and biofilm formation in approximately 1 hour has been developed using commercially available fluorescent-conjugated antibodies and confocal laser scanning microscopy. This methodology has demonstrated that CLSM preparation and imaging of explants can yield rapid and accurate The determination of explant infection occurs in a fraction of the time of conventional culture/polymerase chain reaction-based techniques.

By using the subject technology, one can determine where bacterial biofilms are commonly located such as within the head cavity and adjacent neck of screws, and tissue within the irregular surfaces of bone cement. The visualization and quantification of bacterial colonization within the complex microstructure of orthopaedic hardware is fast and accurate. It is envisioned that the subject technology can be performed during surgery to provide feedback to the surgeon. As such, the surgeon can tailor the infection fighting remedies to target the particular areas and types of infections present rather than hope for the best with system level treatments.

Advantageously, the subject methodologies for the detection of microbial presence on orthopaedic implants do not require successful culture of bacteria from tissue surrounding the implant, which is prone to providing false-negative results for slow growing bacteria like *Propionibacterium acnes* which may take many days to appear in culture. The subject technology provides a base for the development of rapid-detection methods, which will provide visual data within a short time of sample acquisition so that surgeons can determine a course of action while the patient is still on the operating table. In short, the development of a clinically-relevant rapid detection assay for the visualization and quantification of microbial colonization and biofilm formation on orthopaedic explants as taught herein will prove vital in improving orthopaedic interventions, expediting infection diagnosis, and refining treatment that will greatly improve patient outcome.

Bacterial Classification: Gram Staining

Gram testing is used stain in microbiology because of its ability to differentiate between gram-positive and gram-negative species—the two major groups of bacterial classification. Gram testing allows clinicians to distinguish between the two major classes of bacteria, develop an initial diagnosis, and initiate therapy based on inherent differences in the bacteria. The structural differences between these two species (and the subsequent clinical decisions that are made based on a bacterial classification) form a molecular foundation of the subject FCBA and CLSM methods.

The Gram test includes fixation of specimen. After fixation of a specimen to a slide (by heating or alcohol), the sample is exposed to crystal violet dye, and iodine is added to form a complex with primary dye. During subsequent decolorization with alcohol, this crystal violet complex is retained in gram positive bacteria but lost in gram negative ones. Because of this decolorization, upon counterstaining with the Safranin stain gram-negative, bacteria will turn red. This difference in staining is due to differences in these two types of bacteria's cell wall structure, components, and function. For gram-positive bacteria, the initial crystal violet stain gets trapped in a thick, cross-linked mesh-like structure called the peptidoglycan layer. Gram-negative bacteria have a thin peptidoglycan layer that fails to retain the stain, so the cells are counterstained red upon introduction of Safranin dye.

A background on the structural differences between gram-positive and gram-negative species, as well as details on the two specific bacterial organisms used in our investigation, follows. The differences between gram-positive and gram-negative bacteria not only inform the ability to differentially label and identify them with fluorescently conjugated antibodies, but also provide insight on the epidemiological landscape and clinical treatment of these varying species in orthopaedic infection.

Figure 3A:
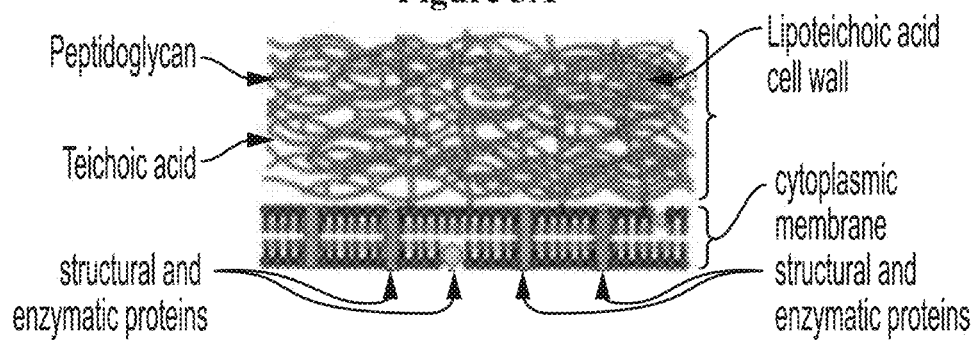
FIGS. 3A and 3B are schematic views of gram-positive and gram-negative bacteria, respectively in accordance with the subject disclosure.
Figure 3B:
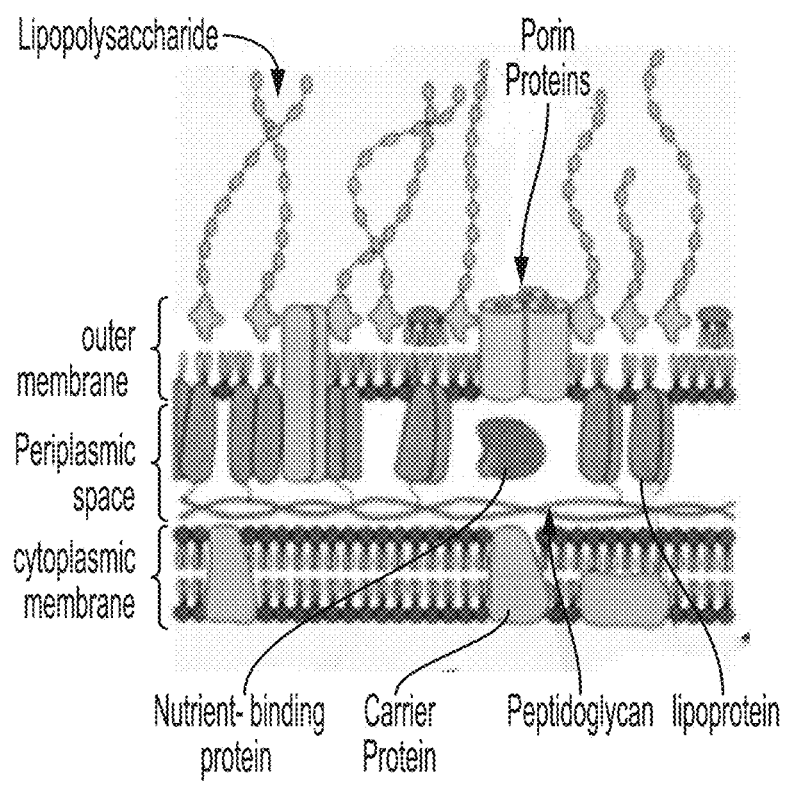

Referring now to FIGS. 3A and 3B, schematic views of gram-positive and gram-negative bacteria, respectively, are shown to illustrate the differences. In FIG. 3A, the gram-positive bacterium consists of a thick cross-linked peptidoglycan layer, interspersed with teichoic and lipoteichoic acid. The lipoteichoic acid, or LTA, is what our gram-positive FCBA antibody binds to. In FIG. 3B, the gram-negative bacterium has a more complex cell wall, consisting of a thin peptidoglycan layer and an outer membrane that contains lipopolysaccharide, phospholipids, and proteins. The gram-negative primary FCBA binds to the lipopolysaccharide (LPS) contained in gram-negative cell walls.

Gram-Positive Bacterial Species: Background

A gram-positive bacterium has a thick peptidoglycan layer that surrounds the cytoplasmic membrane as a mesh-like exoskeleton. The peptidoglycan consists of N-acetylglucosamine and M-acetylmuramic glycan chains that are cross-linked by peptide bridges. This rigid construction provides structure for the cell, as well as protection from the environment. The peptidoglycan layer also includes techoic and lipotechoic acids. Techoic acid consists of the compounds polyribitol phosphate and glycerol phosphate, which are water-soluble polymers that are essential to cell viability. Lipoteic acid is lipid-linked teichoic acid (e.g., the lipoteic acid contains a fatty acid component) and is anchored on the cytoplasmic membrane. Both of these compounds are linked to the peptidoglycan layering and are responsible for cell wall strength, calcium sequestration, and innate host protection activation. Additionally, these compounds are common surface antigens that distinguish bacterial types and promote attachment on mammalian cell surfaces (adherence). Besides being an integral aspect of gram-positive cellular structure and function, lipoteic acid holds added significance because our assay's primary antibody for gram-positive bacterial identification (Gram Positive Bacteria LTA Antibody) targets the lipoteic acid within the peptidoglycan cell walls of gram-positive organisms.

Experimental Gram Positive Species: *Staphylococcus aureus*

*Staphylococcus aureus* (*S. aureus*) is the gram-positive bacterial species that was utilized for in-vitro control and validation studies of the subject technology. In concert with the selected gram-negative species, cultures of *S. aureus* were used to investigate the feasibility of FCBA and CLSM to accurately label gram-positive bacteria, as well as test dilutions and protocol revisions to our antibody-labeling procedure. *Staphylococcus aureus* is a leading cause of biomaterial-associated infections, and a major impetus behind poor post-operative outcomes and revision surgeries. In several studies investigating the prevalence of varying bacterial strains in osteomyelitis, *staphylococci* species (particularly *S. aureus*) were the most commonly isolated organisms.

The high infection rate of *S. aureus* is a multifactorial problem. *Staph aureus* can colonize, adhere, and consequently infect the wound site via exposure of the site to the external environment during injury in the case of an open fracture. Furthermore, these organisms can survive on dry surfaces for extended periods of time because of their thick peptidoglycan layer and absence of an outer membrane. Additionally, *Staphylococcus* is common in the external environment—regularly found on the skin and human mucosal surfaces—and can be introduced to the fracture site during operation via the surgeon, implant, or surgical tools. It is commonly believed that "approximately 15% of normal healthy adults are persistent nasopharyngeal carriers of *S. aureus*, with a higher incidence reported for hospitalized patients, medical personnel, persons with eczematous skin diseases, and those who regularly use needles, either illicitly or for medical reasons."

Adding to the pervasiveness, *S aureus* bacteria are capable of producing a biofilm of monosaccharide, proteins, and small peptides that effectively binds the bacteria to tissues and foreign bodies, such as implants. Orthopaedic trauma patients are at particularly higher risk of infection. *S. aureus* is an extremely pervasive species in orthopaedic infection. Thus, *S. aureus* is an excellent candidate as the gram-positive species to investigate the accuracy and efficacy of the subject technology gram-positive bacterial antibody labeling technique.

In-Vivo Gram-Positive Bacterial Species of Interest: *Propionibacterium acnes*

Another commonly encountered bacterium in orthopaedic infection is *Propionibacterium acnes*, which has high infection rates particularly in shoulder surgery. *Propionibacterium acnes* is also difficult to detect. *Propionibacterium acnes* is an anaerobic, slow-growing gram-positive bacillus that dwells as normal flora in the hair follicles of the dermal skin layers. *Propionibacterium acnes* is commonly found in the head and shoulder region, and has been implicated as the chief causative pathogen in postoperative infection in shoulder arthoplasty and open shoulder procedures because of its high concentration around the skin of the shoulder. *Propionibacterium acnes* may be responsible for between 50-86% of postoperative infection in shoulder surgery.

Because *Propionibacterium acnes* anaerobically lives in deep skin layers, pre-operative sterilization measures can fail to kill indwelling bacteria, leading to bacterial introduction into the wound site when surgery commences. Two presentations, both clinically challenging, are common in *Propionibacterium* infection. One presentation is acute and purulent (pus-producing) and one presentation is late (e.g., years after surgery) which leads to slow implant loosening and surgical failure. Compounding the challenge of high infection rates, the outcomes after treatment of *P. acnes* are also extremely poor. In one investigation, after surgical and antibiotic treatment of *P. acnes* after rotator cuff repair, 38% of patients reported unsatisfactory results at a mean of eight years.

The difficulty in potential *P. acnes* infection treatment, prophylactically and directly, extends beyond the ability of *P. acnes* to simply invade the operative site and provoke infection. *P. acnes* is perhaps even more difficult to properly isolate and identify using the traditional "culture and isolation" method of infection testing. *P. acnes* has a low virulence and unconventional microbiological test required for identification have led to the under-reporting of joint colonization with the organism. Gram staining has been found to unreliably identify *P. acnes* in clinical cultures, leading to false-negative test results that severely impact post-surgical outcomes. Even if the bacteria is properly cultured, isolated, and grown in the lab, it may take days for growth to appear and weeks for colonies to develop. Furthermore, contamination of the sample is common. Care must be taken to avoid contamination of the specimen with the organisms normally found on the skin. With the difficulties in surgery, post-operative treatment, and infection detection that *P. acnes* prompts, the subject technology is a critical improvement in how to rapidly and accurately identify *P. acnes* bacterial colonization at the wound site and/or on the orthopaedic hardware.

Shoulder surgery, whether arthroscopic or open, presents a unique challenge and proof-of-principle opportunity for the development of a rapid-detection assay for gram-positive and/or gram-negative bacterial colonization detection. Rather than simply submit cultures to the lab and wait a number of days for results, surgeons would greatly benefit from a test in accordance with the subject technology that can, within about thirty minutes of submission of surrounding tissue or an explant to the lab, accurately impart to them the infection status of the patient's surrounding tissue, hardware, or wound. This invaluable information would allow the surgeon to make informed treatment decisions such as whether to proceed as a one- or two-stage revision, how much irrigation and debridement to undertake, and/or what antibiotic regimen to prescribe, while the patient is still on the operating table.

Gram-Negative Bacterial Species: Background

Gram-negative bacterial cell walls are more complex than those of gram-positive cells. As opposed to the thick extracellular peptidoglycan layer, a gram-negative cell wall contains two layers external to the cytoplasmic membrane. Immediately surrounding the cytoplasmic membrane is a thin peptidoglycan layer, which contains only 5-10% of the cell wall by weight. External to the peptidoglycan layer is the outer membrane, which provides the outer envelope for the space between the peptidoglycan and membrane layers called the periplasmic space. The perisplasmic space contains components of transport systems for ions and metabolites, as well as a mélange of metabolic enzymes. The outer membrane, unique to gram-negative bacteria, maintains bacterial structure and acts as a permeability barrier to large molecules. This outer layer is composed primarily of lipopolysaccharide, or LPS, which is vital to the antibody labeling system. Because LPS (and the outer membrane which it constructs) is unique to gram-negative bacteria, it serves as the ideal target molecule for our primary bacterial antibody responsible for labeling gram-negative species. In one embodiment, the gram-negative bacteria effectively targets and binds to LPS within the outer membrane of gram-negative cells. Additionally, neither the gram-negative peptidoglycan layer nor the outer membrane contains teichoic or lipoteichoic acids. Because of these individualized features of gram-negative and gram-positive cells, specific antibody labeling can be achieved for each type without overlap or "cross-talk" labeling between Gram classifications.

Experimental Gram Negative Species: *Acinetobacter baumannii*

In one embodiment, a gram-negative experimental equivalent to *S. aureus, Acinetobacter baumannii* was selected as the gram-negative control species utilized for FCBA dilution testing as well as protocol validation, troubleshooting, and refinement. Glass-bottomed well plates were inoculated with a standard concentration of bacteria, cultured, and fixed to enable antibody-labeling experimentation. *A. baumannii* is quickly becoming a prominent concern in nosocomial orthopaedic infection due to it's pervasiveness and antibiotic resistance. *Acinetobacter* is able to survive on both moist and dry surfaces, such as human skin, a feature unusual for gram-negative rods. These bacteria are also part of the normal oropharyngeal flora of some healthy people and can proliferate to large numbers during hospitalization.

*Acinetobacter* is an opportunistic pathogen that causes infections in the respiratory tract, urinary tract, and wounds, which can lead to septicemia. These nosocomial wound infections are particularly problematic because many *A. baumannii* infections are caused by strains resistant to most antibiotics. Pan-resistant strains have been documented that are resistant to treatment, the drug of last resort for many gram-negative infections.

Beyond the scope of civilian orthopaedic trauma, *Acinetobacter* is an even larger threat in military operations. During combat operations, extremities continue to be the most common sites of injury with associated high rates of infectious complications. Many patients with extremity injuries develop osteomyelitis, and many of those infections relapse or recur. The bacteria infecting those wounds have included multidrug-resistant bacteria such as *Acinetobacter baumannii*". With increasing prominence as a gram-negative pathogen encountered in orthopaedic infection, *A. baumannii* effectively fit the role as a clinically relevant gram-negative organism. As such, *A. baumannii* was used in testing and refinement of the subject technology.

Fluorescently-Conjugated Bacterial Antibodies

Method in accordance with the subject technology fluorescently conjugate bacterial antibodies (FCBA) as a means to label target cells and accurately identify bacterial adherence constructs. The method can accurately and rapidly test explanted orthopaedic hardware for the presence of bacterial adhesion or biofilm formation is empowered by the tools of FCBA and confocal laser-scanning microscopy, or CLSM. Utilizing these techniques, the method can effectively distinguish between gram-positive and gram-negative bacterial species on orthopaedic trauma explants.

A cornerstone of FCBA experimentation is the knowledge of how these antibodies operate. Molecules that are capable of fluorescing are called fluorescent dyes, or fluorochromes. If a fluorochrome is conjugated to a macromolecule, that tagged macromolecule is said to contain a fluorophore, capable of producing fluorescence. In the case of FCBA technology, carefully chosen fluorochromes are conjugated to bacterial antibodies that bind to specific target elements of a cell type. This conjugation of fluorophore to antibody is achieved through either a chemical reaction or by simple adsorption. The coupling of fluorochromes to antibodies forms the basis of staining with labeled antibodies.

Figure 4A:
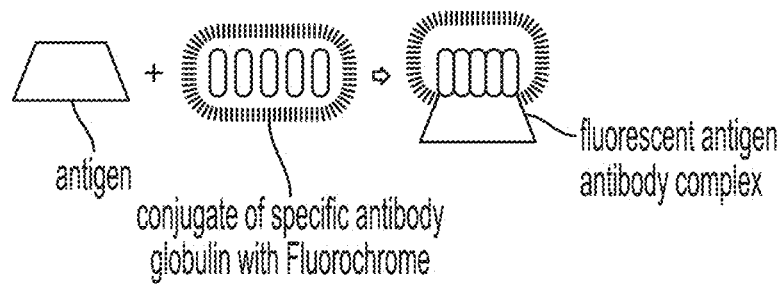
FIGS. 4A and 4B are diagrams that illustrate labeling processes of direct IF and indirect IR staining in accordance with the subject disclosure.
Figure 4B:
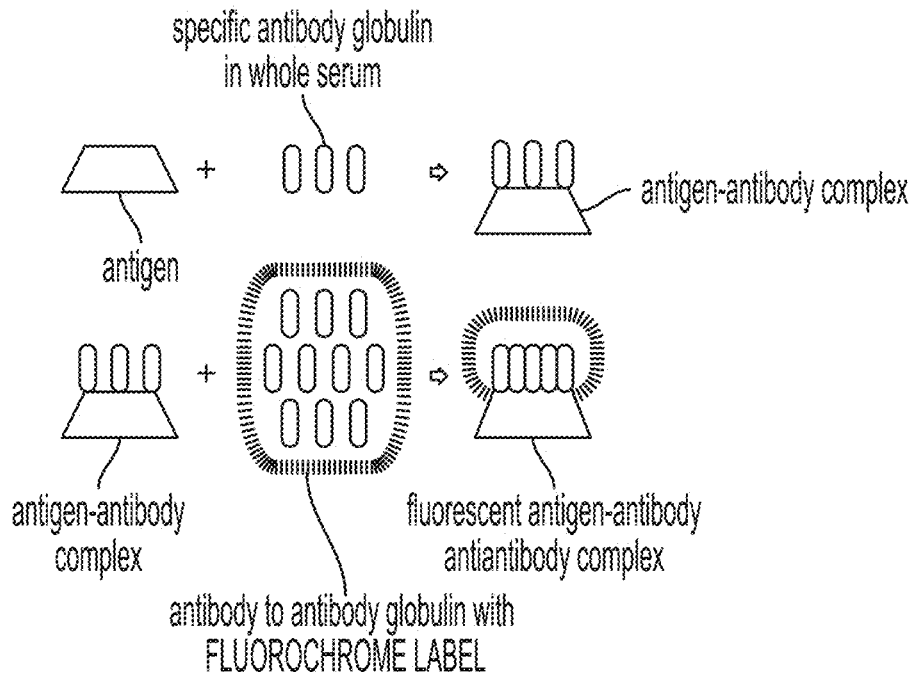

Referring now to FIGS. 4A and 4B, diagrams that illustrate labeling processes of direct IF and indirect IR staining are shown. The first method of FIG. 4A, referred to as "Direct Immunofluorescent Staining," consists of applying an already-combined mixture of fluorochrome and antibody to a sample containing the antigen target. Once this "conjugated" FCBA is introduced and given time to adhere to its target, the sample is ready for imaging with CLSM. The second method of FIG. 4B, called "Indirect Staining," consists of first treating the sample containing the antigen target with unlabeled specific antiserum, or "primary antibody". The resulting antigen-antibody is rendered visible by treating it with a "secondary antibody," a fluorescent-labeled antibody to the specific antibody globulin. Once the secondary has hound to the primary antibody, the sample is ready for imaging.

Fluorescence and Associated Imaging Phenomena

The samples are ready for imaging once the adhered antibody (either by direct or indirect methodology) has fluorescence. Fluorescence is the emission of photons by atoms or molecules whose electrons are transiently stimulated to a higher excitation state by radiant energy from an outside source. When a fluorescent molecule absorbs a photon of the appropriate wavelength, an electron is excited to a higher energy state and almost immediately collapses down its initial ground state. In the process of energy collapse, the molecule can release the absorbed energy as a fluorescent photon.

Fluorescence is instigated by the light source of the confocal microscope, which is subsequently captured and analyzed. Because FCBAs fluoresce at different wavelength ranges, multiple fluorophores can be detected in the same sample. Despite the incredible technology behind FCBA, a number of challenges must be overcome. One challenge overcome by the subject technology includes the phenomena of quenching, photobleaching, bleedthrough, and autofluorescence.

Both quenching and photobleaching reduce the amount of fluorescence in the sample, which can interfere with clear visualization and characterization. Quenching occurs because of charge-transfer interactions with nearby aromatic amino acids, while photobleaching refers to the permanent loss of fluorescence by a dye due to photon-induced chemical damage and covalent modification. To prevent quenching, care must be taken to allow for proper adherence and binding of each individual antibody to the indicated target molecules in the sample. To prevent photobleaching, tin foil may be wrapped around the sample at all times throughout confocal preparation protocol to prevent light-induced damage to any of the antibodies.

Autofluorescence is another FCBA challenge. All cells contain endogenous metabolites that fluoresce when illuminated with the confocal microscope light source. Some common sources of autofluorescence are B vitamins, flavins, reduced pyridine nucleotides, fatty acids, porphyrins, and uncoupled cytochromes. The fluorescence of these cellular elements (and others) adds to the background signal in the microscope. In some cases these signals are strong enough to be mistaken for the signals of fluorescently tagged molecules. Under the microscope the metallic surfaces also contributed a degree of "background", in addition to residual cellular elements or surgical artifact. To accomplish the clearest image possible, a number of "blocking" steps may be added in order to mitigate the fluorescence of elements besides the desired target.

Another challenge of FCBA imaging is that of bleedthrough. Bleedthrough occurs when one fluorescence signal (e.g., from a flouorophore) crosses over and interferes with the fluorescence signal of a different fluorophore, causing interference and "cross-talk" between the desired colors in the sample. Bleedthrough can be minimized with multiple iterations of antibody dilution testing in bacterial plates to ensure balanced fluorescence between antibody types (e.g., gram positive and gram negative primary and secondary). Correct dilutions of the primary and secondary antibodies facilitates antibody-specific tagging and fluorescence on the desired target and decreased crosstalk with other FCBA's in the sample. Respective secondary antibodies (the fluorescently conjugated antibody) with different excitation and emission wavelengths, or fluorescence ranges, can be chosen to minimize bleedthrough in the sample.

Confocal Laser Scanning Microscopy

Referring now to FIG. 5, a system for confocal laser scanning microscopy (CLSM) is shown. A typical CLSM includes a fluorescent microscope, multiple laser light sources, a confocal scan head with optical and electronic equipment, a computer monitor for display, and software for acquiring, processing, and analyzing images. An understanding of how CLSM works helps for proper comprehension of CLSM and FCBA as an attractive tool for rapid infection detection. Although the technology behind CLSM is complex, imaging of the sample is achievable.

An excitation filter selectively transmits short wavelengths for exciting a specific fluorophore in the specimen. A dichromatic mirror reflects the short wavelength light towards the objective and specimen, while transmitting long wavelength returning fluorescent light toward the detector. The mirror also directs any excitation wavelengths reflected by the specimen back toward the filter and illuminator. Finally, the barrier filter blocks any residual wavelengths. The fluorescent wavelengths through these filters then form an image on the eye or camera.

There are many advantages of using CLSM as a tool for visualizing and analyzing explanted hardware for potential bacterial adhesion or biofilm formation. "By using a motor that changes the microscope focus in small steps along the z-axis, confocal makes it possible to acquire a stack of images, or z-series, at different focal planes and generate a three-dimensional view of the specimen using computer software.

The capability for a three-dimensional rendering of the explants or tissue surface allows for a clear visualization of whether and where bacterial adhesion and/or biofilm is present. The CLSM can also simultaneously scan for multiple fluorescence wavelengths. Additionally, the CLSM allows for quick scanning of an explant surface, regardless of any microtopography or surface imperfections. CLSM software allows for quantification of bacterial load/coverage in a given image or sample, potentially enabling more concrete discussions with clinicians regarding infection status.

Bacterial Cell Culture

Single colonies of methicillin-sensitive *Staphylococcus aureus* and multi-drug resistant *Acenitobacter baurnannii* were respectively suspended in Bacto Tryptic Soy Broth media (available from Becton and Dickinson of Sparks Md. A SpectraMax spectraphotometer (available from Molecular Devices of Sunnyvale Calif.) was used to take the optical density of the bacterial stock. Using aseptic technique, 35 mm glass bottom well plates (available from MatTek of Ashland Mass.) were inoculated with 2 mL of a standard bacterial concentration of $2 \times 10^7$ colony forming units per mL (CFU's/mL). The plates were incubated for 24 hours at 37° C., with fresh TSB media added at 4 hours.

Eukaryotic and Dual-Bacteria Co-culture

Human calavarial osteoblasts (HCO) (available from ScienCell of Carlsbad, Calif.) were cultured in Osteoblast Basal medium (ObM-b) (available from ScienCell of Carlsbad, Calif.) supplemented with 10% Fetal Bovine Serum and incubated at 37° C., 5% CO2 in a humidified atmosphere until 65% confluent. HCO cells were cultured at 50,000 cells/mL in glass-bottomed 35 mm dishes (available from MatTek of Ashland, Mass.) overnight. Bacteria were added at a concentration of $2 \times 10^7$ CFU's/mL and allowed to adhere for 2.5 hours. The co-cultures were then fixed and prepared for CLSM as detailed below.

Bacterial Fixation and Confocal Laser Scanning Microscopy Preparation

After 24 hours of incubation, the bacterial 35 mm glass bottom well plates were removed from the incubator and fixed in 100% acetone for 30 minutes. The plates were then washed three times with 1x phosphate-buffered saline+1% Rabbit Serum (10xPBS, available from Hoefer Inc. of San Francisco Calif.). Next, undesired antibody-binding/labeling effects were inhibited via the blocking step. A solution of 50% Bovine Serum Albumin (BSA, available from BD Biosciences of San Diego Calif.)+50%. Rabbit Serum was introduced to the plates for 30 minutes, and the plates were placed on a rocker for gentle washing effect at 30 rpm. Once blocking was achieved, the plates were prepared for CLSM according to the FCBA protocol detailed in the below section.

Confocal Laser Scanning Microscopy Explant Preparation Assay

For testing, explants of various compositions were collected and immediately stored in a 10% neutral buffered fonnalin solution until labeling. At the outset of preparation, these explants were washed three times in PBS+1% Rabbit Serum to remove formalin. First, Gram-positive LTA (available from ThermoFisher Scientific of Rockford Ill.) at 1:100 dilution was introduced as the gram-positive primary antibody for 60 minutes. Samples were then washed twice with PBS+1% Rabbit Serum. [Rabbit Anti-Mouse IgG, Fe Fragment Specific, Fluorescein Conjugated Secondary] was utilized as the secondary gram-positive antibody (available from ThermoFisher Scientific of Rockford Ill.) and introduced at 1:50 for 60 minutes. Samples were then washed twice with PBS+1% Rabbit Serum. [LPS gram-negative] (available from Acris Antibodies of Herford Germany) was utilized as the gram-negative primary antibody at 1:1000 for 60 minutes. After two PBS+1% Rabbit Serum washes, the gram-negative secondary [Alexa Fluor 586) (Life Technologies, Grand Island N.Y.) was introduced for 60 minutes at 1:200. The samples were placed in fresh PBS and were then ready for CLSM imaging. As can be seen in FIG. 6, exemplary gram positive fluorescein isothiocyanate (FITC) shows green (Ex 492 nm-EM 518 nm) and gram negative Alexa Fluor shows red (Ex 578 nm-Em 603 nm).

Confocal Laser Scanning Microscopy Explant Preparation: Rapid Assay

The subject technology includes a rapid detection assay using the same product and dilutions as detailed above. Explants are washed three times with PBS+1% Rabbit Serum, and blocked with a solution of 50% Rabbit Serum+ 50% BSA for 15 minutes. The gram-positive and gram-negative primary antibodies are vortexted together for solution homogeneity then introduced to the specimen for 15 minutes. After two PBS+1% Rabbit Serum washes, the gram-positive and gram-negative secondary antibodies are vortexed together for solution homogeneity and introduced to the specimen for 15 minutes. After introduction of the antibodies, the sample is washed in fresh PBS and was then ready for CLSM imaging.

Gram Positive+Gram Negative CLSM Assay: 4 hours 45 minutes

The following steps are performed:
1) 3×PBS+1% RS washes;
2) Block with BSA+RS, 30 minutes;
3) Introduce grain-positive 1° [gram-positive LTA] 1:100, 60 minutes;
4) 2×PBS washes+1% RS washes;
5) Introduce gram-positive 2° [rabbit anti-IgG Fc FITC] 1:50, 60 minutes;
6) 2×PBS+1% RS washes;
7) Introduce gram-negative 1° [LPS gram-negative anti-goat] 1:1000, 60 minutes;
8) 2×PBS+1% RS washes;
9) Introduce gram-negative 2° [Alexa Fluor 568] 1:200, 60 minutes;
10) 2×PBS+1% RS washes; and
11) Replace with fresh PBS, ready for confocal.

Confocal Laser Scanning Microscopy Visualization and Analysis

Once ready for CLSM, samples are placed on glass slides and mounted with a single drop of Vectashield+DAPI medium (available from Vector Laboratories Inc. of Burlingame Calif.). Vectashield prevents against photobleaching and rapidly provides 4',6-diamidino-2-phenylindole (DAPI) for eukaryotic labeling. CLSM visualization and analysis occurs, preferably using a Nikon Clsi confocal laser microscope with three diode lasers at wavelengths 402, 488, and 561. Deconvolution (an algorithm that eliminates background and provides a truer image of the specimen) is carried out by Elements Software (available from Nikon of Melville N.Y.).

Quantification

Once CLSM images are acquired, quantification is accomplished using ImageJ software (available from NIH of Bethesda Md.). The image is separated into Green, Red, and Blue channels, indicating respective presence of gram-positive, gram-negative, and eukaryotic cells respectively as shown in FIGS. 7A and 7B, which are CLSM images separation by fluorescent signals. Threshold saturation determination of observed eukaryotic staining is pictured in FIG. 7A while grayscale of green channel with visible cocci is shown in FIG. 7B. Within each channel, a saturation threshold is determined by modulating the saturation of each color, in order to isolate completely labeled and identifiable objects and mitigate background and autofluorescence. Once the threshold is chosen, the relative areas of coverage for each color channel is determined, along with standard deviation. Total cellular coverage was also computed.

Results

The subject technology provides a visual means of identifying and characterizing bacterial biofilm presence on explanted orthopaedic hardware. Many FCBA tagging approaches can be utilized. The following results detail various steps divided into phases, and within each phase particularly notable Explants studies from that respective step are included.

Individually cultured and fixed plates of Methicillin-sensitive S. aureus and multi-drug resistant A. baumannii were utilized for testing. These bacterial plates provided a template with which modifications to bacterial concentrations, antibody dilution strengths, and labeling times could be studied and evaluated in order to optimize the subject methodologies. Next, explants were subjected to the established CLSM preparation protocol, the results of which demonstrated the necessity for further protocol refinement due to issues in FCBA cross talk and autofluorescence. Troubleshooting was achieved through a bacterial co-culture model in which MSSA (gram-positive) and A. baumannii (gram-negative) were cultured together in glass bottom well plates and fixed.

Once ready for CLSM preparation, these co-culture plates were subjected to many manipulations of the FCBA assay in order to optimize for clear visualization of both gram species simultaneously with no overlap. Once this was achieved, explant preparation and analysis was reinitiated. In concert with an affiliated eukaryotic/bacterial cell culture and CLSM preparation project, the CLSM protocol was further refined for time optimization.

Phase 1: Proof of Principle and CLSM/FCBA Protocol Refinement in Single-Species Plates Initial plates demonstrated several challenges encountered with fluorescent tagging from the outset. Images were taken from two separate lots of A. baumannii gram-negative FCBA control studies. A number of factors could have contributed to these resultant images which did not provide reliable results, including improper inoculation, fixation, blocking, and/or FCBA dilution and exposure times. Through iterations of experimental modifications (and constructive analysis of results like these), the subject technology was refined for improved results.

Quantification was provided as follows
A. baumannii control 120× (7A);
Total bacterial coverage: 0.145±10.88% Red threshold: 0.26%;
A. baumannii control 120× (7B); and
Total bacterial coverage: 0.367±0.0567% Red threshold: 0.52%.

Figure 8A:
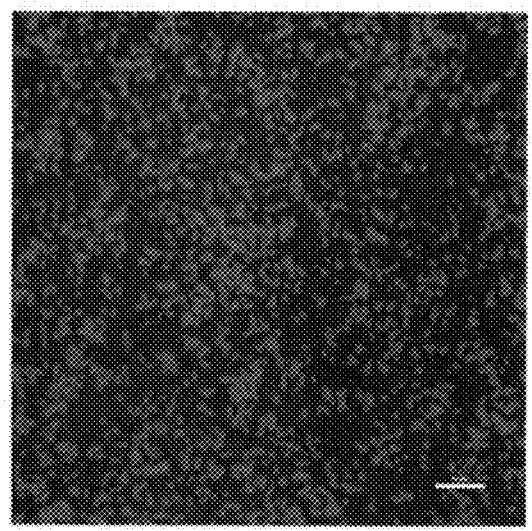
FIGS. 8A and 8B are images of successfully cultured, fixed, CLSM-prepped, and imaged bacterial plates in accordance with the subject disclosure.
Figure 8B:
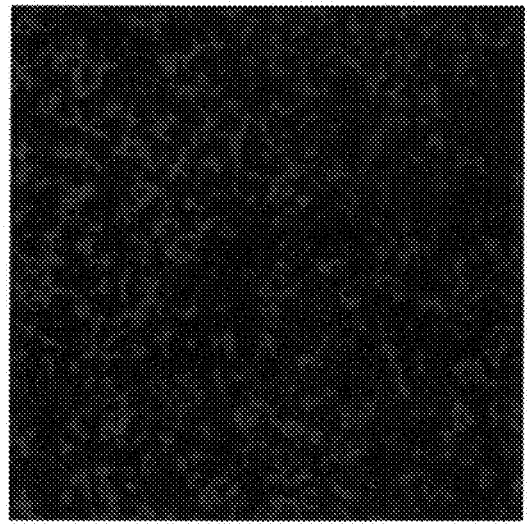

Referring to FIGS. 8A and 8B, successfully cultured, fixed, CLSM-prepped, and imaged bacterial plates are shown. FIG. 8A is S. aureus (gram positive, FITC green) and FIG. 8B is multi-drug resistant A. baumannii (gram negative, Alexa Fluor 568, red). Note the cocci (spherical) shape of each species and relative size. These established controls acted as essential references for ensuing protocol refinement and CLSM image analysis.

Quantification is as follows:
MSSA control 120× (8A)
Total bacterial coverage: 20.88±0.582%
Green threshold: 21.32%
A. baumannii control 120× (8B)
Total bacterial coverage: 39.268±0.462% Red threshold: 39,17%

S. aureus-specific CLSM Preparation Assay: 2 hours
1. 3×5 minute PBS wash
2. Block with BSA, 30 min
3. Introduce [S. aureus/FITC conjugated antibody] 1:200 dilution, 60 min
4. 3×5 min PBS, ready for confocal Gram Negative CLSM Preparation Assay: 3 hours 30 minutes One method for a 3 hour, 30 minute gram negative CLSM preparation assay is as follows:

1. Block with BSA, 30 min;
2. Introduce gram negative 1° antibody [LPS gram negative anti-goat] 1:600 dilution, 60 minutes;
3. 3×5 min PBS wash;
5. Introduce gram negative 2° antibody [Alexa Fluor 568] 1:200 dilution, 60 minutes; and
6. 3×5 min PBS washes, ready for confocal.

Phase 2: Gram Positive Explant Preparation and Critical Analysis

Figure 9:
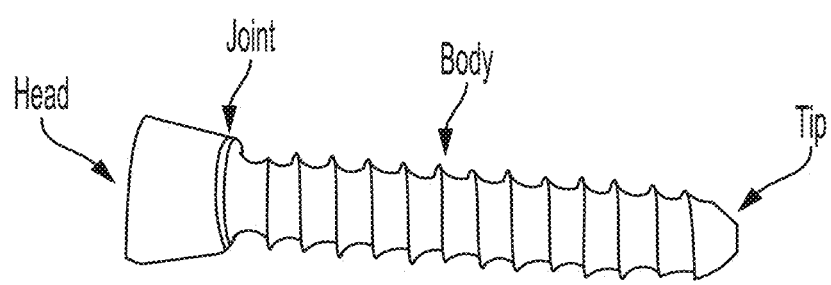
FIG. 9 is an image of a screw with various locations on a screw that can be analyzed for potential biofilm growth in accordance with the subject disclosure.

Once the capability to individually prepare samples and identify bacterial adhesion and was established, preparing and imaging explants was improved. Although a variety of explants were imaged (including screws, nails, plates, and poly-methyl methacrylate bone cement), the most commonly received and imaged hardware was explanted screws. FIG. 9 is an image of a screw with four locations screws that were analyzed for potential biofilm growth.

Except for several cases in which tissue and bacterial cells were detected at the screw joint location, eukaryotic and bacterial cell presence was detected nearly exclusively at the screw head. Without being limited to any particular theory, this is intuitively attributed to the fact that the screw body and tip are secured into native bone, with no exposure to native soft tissue or potential bacterial colonization sites. In order to more definitively gather data about the CLSM assay, explants known to be infected with a specific bacterial species were first prepared and analyzed. This enabled analysis of whether in-vitro control studies translated to successful imaging of explants.

Figure 10A:
FIGS. 10A and 10B are CLSM images that demonstrate bacterial load being present in accordance with the subject disclosure.
Figure 10B:
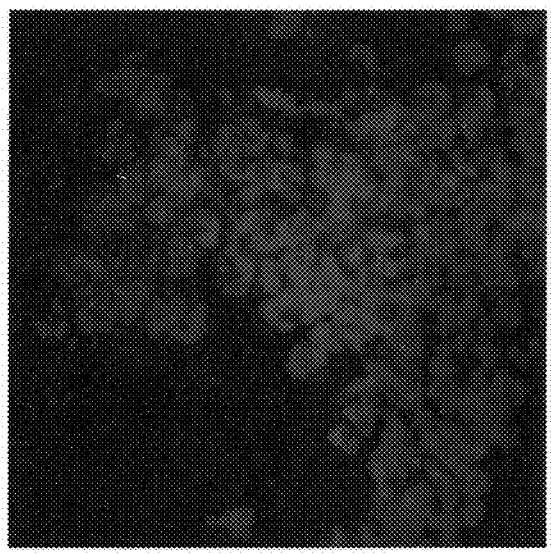

A screw head such as shown in FIG. 1B was known to be infected with *Staphylococcus aureus*. Rather than use the specific *S. aureus* antibody utilized in the in-vitro control plates, the gram-positive primary antibody and it's conjugated secondary fluorophore were used instead in order to more closely simulate the conditions of preparing and analyzing explants that was of unknown potential infection status. Upon examination with CLSM, a large amount of eukaryotic tissue was noted. Though a markedly smaller bacterial load was present (in comparison with the bacterial plate control studies) gram-positive cocci (green) interspersed with the native tissue was observed, confirming the presence of gram-positive bacterial colonization. FIGS. 10A and 10B are images that demonstrate this presence. Similar results were achieved on a number of other explants that were known to be infected with various gram-positive bacterial species, including several other screw heads and a poly(methyl) methacrylate bone cement specimen.

Figure 10C:
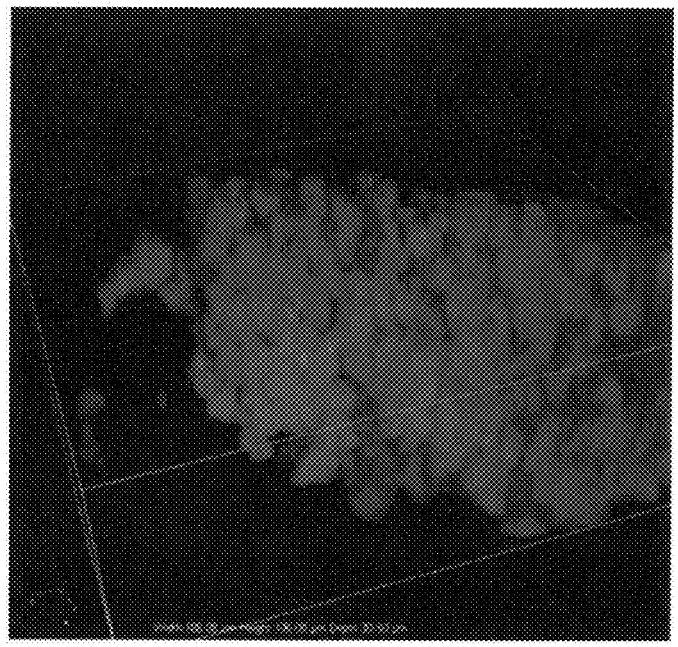
FIG. 10C is a plurality of CLSM images arranged into a complete three-dimensional rendering of the specimen's surface in accordance with the subject disclosure.

The striking images of FIGS. 10A and 10*b* provided the opportunity to utilize the three-dimensional rendering feature of CLSM. CLSM software is able to arrange a sample's z-stacks into a complete three-dimensional rendering of the specimen's surface, in this case a screw head. As seen below in FIG. 10C, the three-dimensional rendering enables another perspective of visualization and characterization.

Gram Positive CLSM Preparation Assay: 4 hours

Below is a recipe for a gram positive CLSM preparation assay of approximately four hours:
1) 3×5 min PBS washes;
2) Block with BSA, 1 hour 30 minutes;
3) Introduce gram positive 1° antibody [gram positive LTA] 1:100, 60 min;
4) 2×10 min PBS washes;
6) Introduce gram positive 2° [rabbit anti-IgG Fc FITC] 1:50, 60 min;
7) Add DAPI, 5 min; and
8) Replace with fresh PBS, ready for confocal.

In testing with such protocol, quantification as performed and the results are below in Table 1.

TABLE 1

| Item | MSAA screw head #1 | MSSA screw head #2 |
|---|---|---|
| Total bacteria coverage | 2.32 +/− 1.132% | 2.134 +/− 1.312% |
| Green threshold | 2.96% | 3.74% |
| Eukaryotic coverage | 41.3 +/− .428% | 34.9 +/− .439% |
| Blue threshold | 41.27% | 34.85% |

Figure 11A:
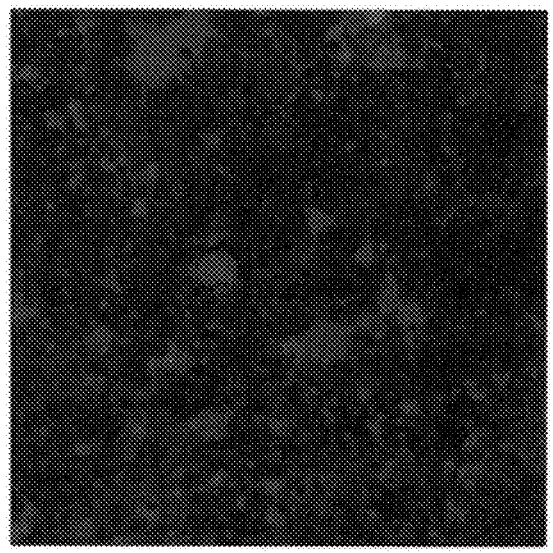
FIGS. 11A and 11b are CLSM images from a titanium and stainless steel screwhead, respectively, that exhibit the CLSM phenomenon of autofluorescence.
Figure 11B:
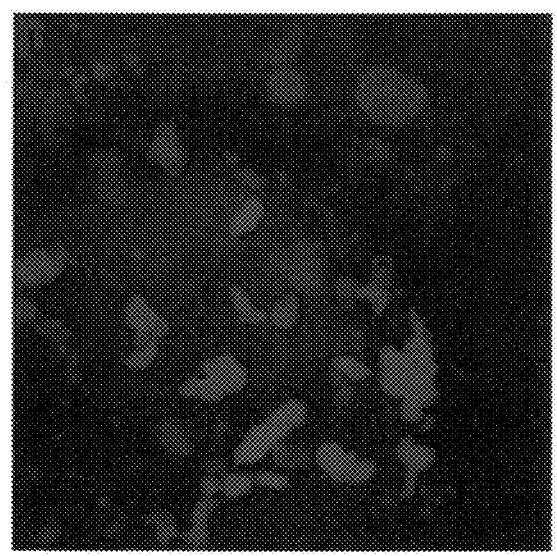

Additional explants below were prepped as detailed in the above "Gram Positive CLSM Preparation Assay," a 4 hour, 10 minute long protocol that specifically labels gram-positive species. Definitive eukaryotic cells are present, along with possible gram-positive biofilm elements and bacteria. FIGS. 11A and 11*b* are images from a titanium and stainless steel screwhead, respectively, that exhibit the CLSM phenomenon of autofluorescence, in which normal cellular elements, residue, and artifact on the specimen surface fluoresces under the confocal lasers. The image in FIG. 11A contains potential gram-positive species (with some discernible coccal morphologies) while the image in FIG. 11B contains larger amounts of background and autofluorescence at a lower signal strength (less bright and less defined morphologies.)

In testing with such protocol, quantification as performed and the results are below in Table 2.

TABLE 2

| | Screw type | |
|---|---|---|
| | Titanium | Stainless steel |
| Total bacterial coverage | 4.14 ± 1.03% | .854 ± .522% |
| Green threshold | 4.55% | 3.40% |

Phase 3: Full Gram Positive and Gram Negative Assay and Critical Analysis

Figure 12A:
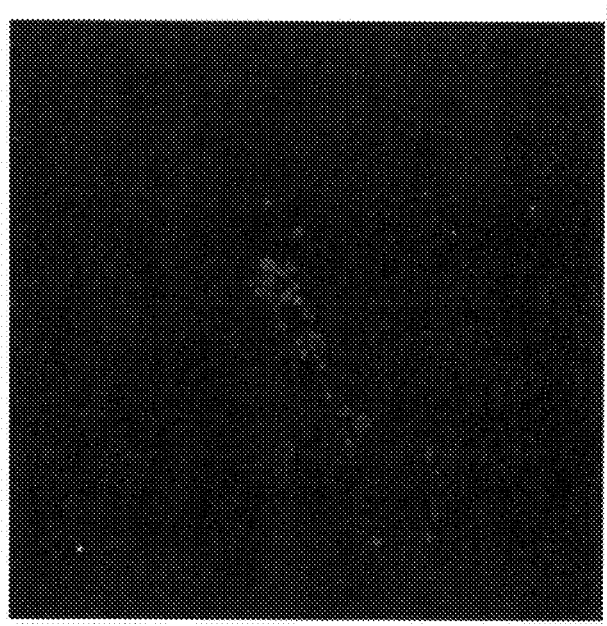
FIG. 12A is a characterization of the resultant images from a screw head in accordance with the subject technology.
Figure 12B:
FIG. 12B is evidence in a CLSM image of a gram-positive infection indicated by thorough coverage of *S. aureus*-sized cocci in accordance with the subject technology.
Figure 12C:
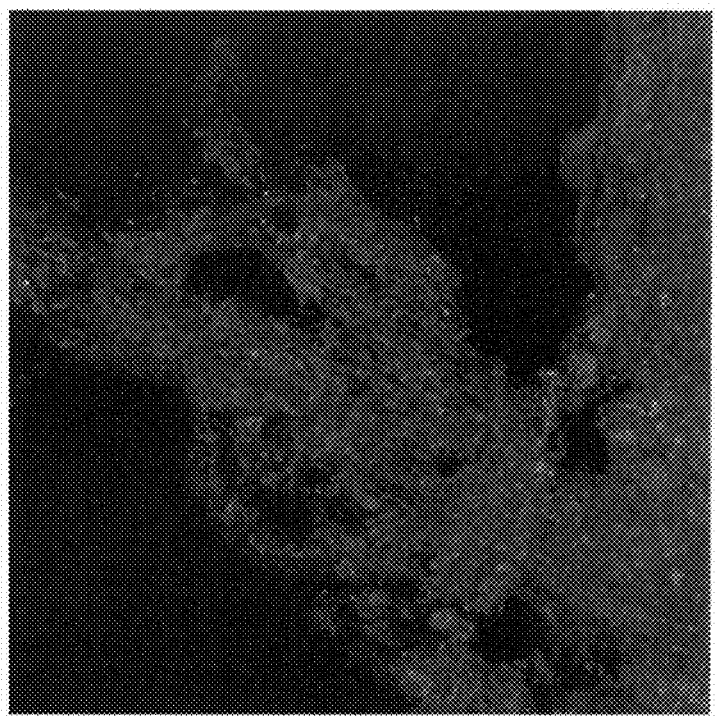
FIG. 12C is a CLSM image that demonstrates the challenges of bleedthrough and autofluorescence in implementation of a full FCBA assay in accordance with the subject technology.

After a number of explants prepared and favorably analyzed with the gram-positive assay, further investigation of the consecutive gram-positive and gram-negative FCBA labeling was conducted. A screw was subjected to the full gram-positive and gram-negative CLSM assay. FIGS. 12A-C are CLSM images of the results. In FIG. 12A, characterization of the resultant images from the screw head was made difficult by undefined morphologies. However, in FIG. 12B evidence of a gram-positive infection is indicated by thorough coverage of *S. aureus*-sized cocci.

The image of FIG. 12C demonstrates the challenges of bleedthrough and autofluorescence in implementation of the full FCBA assay. The image of FIG. 12C exhibits discernible red (gram-negative) and green (gram-positive) cocci. Possible autofluorescence of specimen artifact is indicated, as well as bleed through (odd colors on account of fluorochrome overlap) and background signals (indefinable morphologies also fluorescing).

The Gram Positive+Gram Negative CLSM Assay took approximately 7 hours and the procedure is below:
1) 3×5 minute PBS washes;
2) Block with BSA, 90 minutes;
3) Gram negative 1° [gram negative endotoxin] 1:100, 90 min;
4) 2×10 min PBS washes;
5) Gram negative 2° [Alexa Fluor 594] 1:100, 60 minutes;

6) Gram positive 1° [gram positive LTA] 1:100, 60 min, 1:100;
7) 2×10 min PBS washes;
8) Gram positive 2° [rabbit anti-IgG Fc FITC] 60 min, 1:50;
9) Add DAPI, 5 min; and
10) Replace with fresh PBS, ready for confocal.

In testing with such protocol, quantification was performed and the results are below.

Screw Side 120× (FIG. 12A)
Total gram-positive coverage: 0.378±3.889%
Green threshold: 0.47%
Total gram-negative coverage: 0.048±27.067%
Red threshold: 0.08%
Total eukaryotic coverage: 0.065±5.585%
Blue threshold: 0.09%
Screw Side 120× (FIG. 12B)
Total gram-positive coverage: 0.399±0.4.235%
Green threshold: 0.47%
Total gram-negative coverage: 0.094±16.532%
Red threshold: 0.094%
Total eukaryotic coverage: 0%

Figures 13A, 13D, 13G:
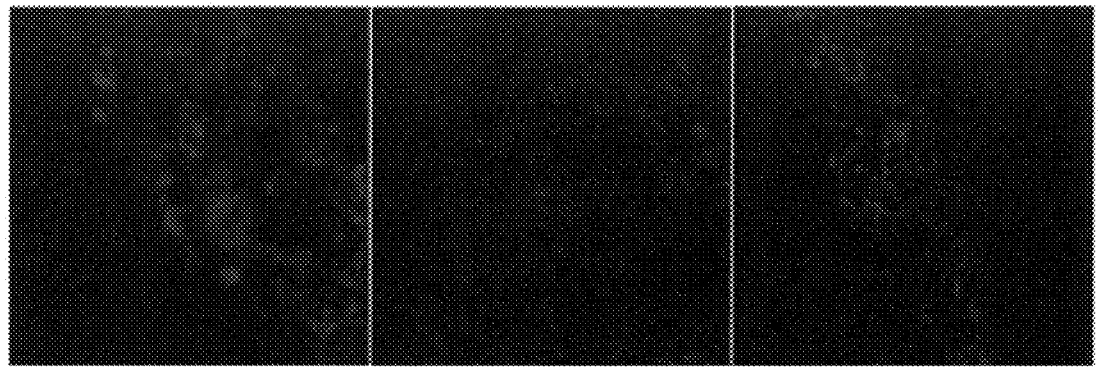
FIGS. 13A-I are CLSM images of a sample in the green channels, red channels, and composites of both channels plus blue staining (DAPI) in accordance with the subject technology.
Figures 13B, 13E, 13H:
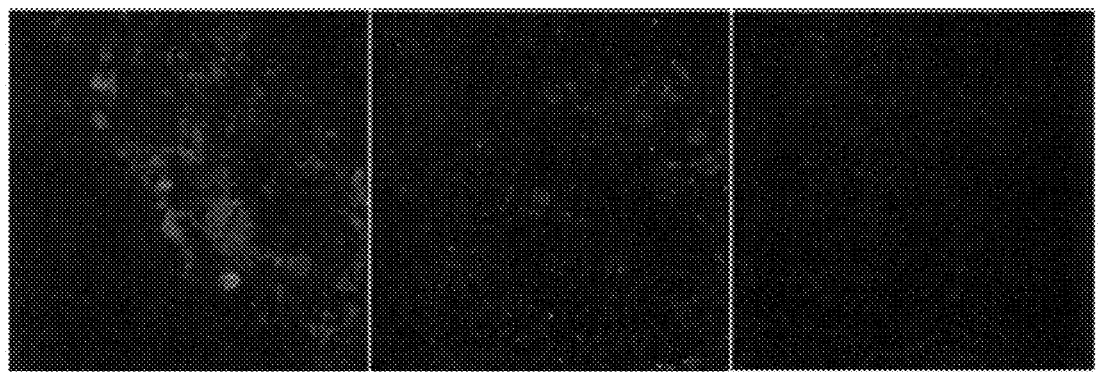
Figures 13C, 13F, 13I:
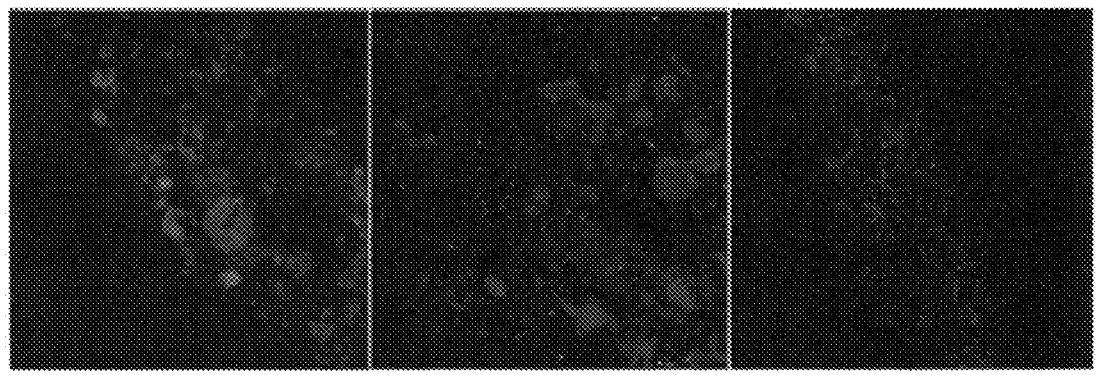

Further experimentation of the combined gram positive and gram-negative assay continued on this screw head as shown in FIGS. 13A-I. The images of FIGS. 13A, 13D, and 13G are images of the screw in the green channel, the images of FIGS. 13B, 13E, and 13H are the same respective images in the red channel, and the images of FIGS. 13C, 13F, and 13I are the composite of both channels plus blue staining (DAPI). The overlap between the red and green channels, as well as the discoloration of potential cocci in the composite image, indicates bleed through.

Phase 4: New Gram-Negative Assay: Controls and Refinement

Figure 14A:
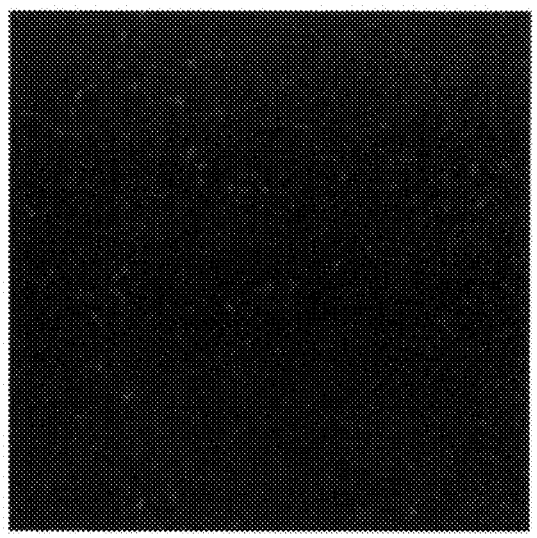
FIGS. 14A and 14B are images of fluorescence of MSSA with application of improperly strong gram-negative antibody in accordance with the subject technology.
Figure 14B:
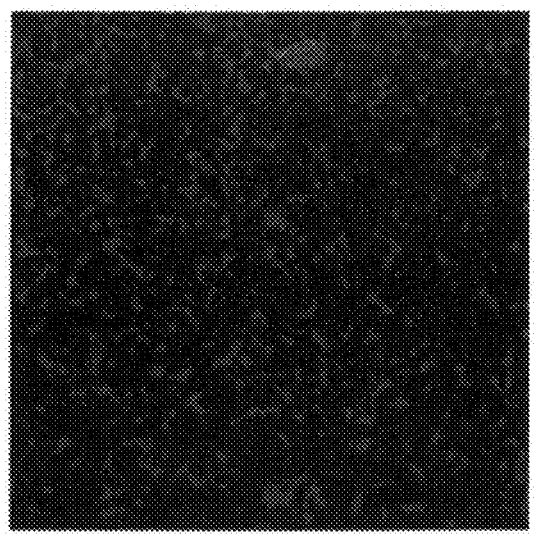

To overcome the assay bleed through, a new gram-negative primary antibody and fluorescently conjugated secondary antibody were acquired. Multi-drug resistant *A. baumannii* was once again used for refinement and assay development, while Methicillin-sensitive *S. aureus* cultures were used to ensure that no undesired cross labeling occurred of the gram negative FCBAs labeling a gram-positive species. At first, the MSSA was fluorescing with application of the gram-negative primary and secondary at both 1:200 and 1:400 dilutions, as detailed in the images of FIGS. 14A and 14B respectively.

The procedure for labeling MSSA with new gram-negative FCBAs took approximately 2 hours 55 minutes and was performed as follows:
1) 3×5 min PBS washes;
2) Block with BSA, 30 min;
3) Introduce gram-negative 1° [LPS gram negative anti-goat] 8=1:200, 9=1:400, 60 min;
4) 2×5 min PBS washes;
5) introduce gram-negative 2° [Alexa Fluor 568] 1:200, 60 min; and
6) Replace with fresh PBS, ready for confocal.

In testing with such protocol, quantification was performed and the results are below.

MSSA tagged with gram-negative FCBAs 1:200, 120× (14A)
Total bacterial coverage: 5.4±1.040%
Red threshold: 5.59%
MSSA tagged with gram-negative FCBAs 1:400, 120× (14B)
Total bacterial coverage: 18.43±0.538%
Red threshold: 19.06%

Figure 15A:
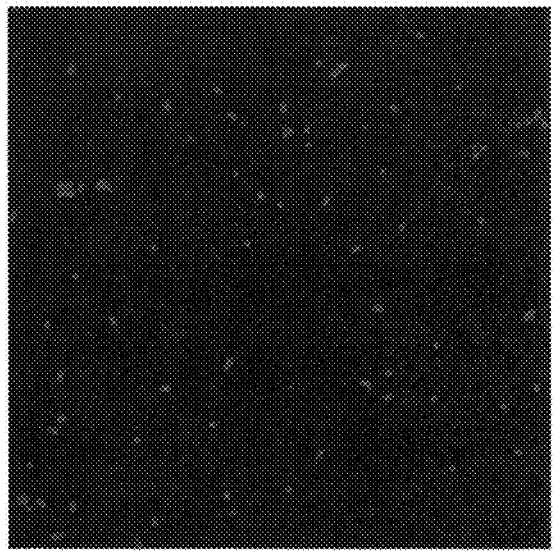
FIGS. 15A and 15B are CLSM images of manipulations of Gram-Negative Antibody Assay on Bacterial Co-Cultures in accordance with the subject technology.
Figure 15B:
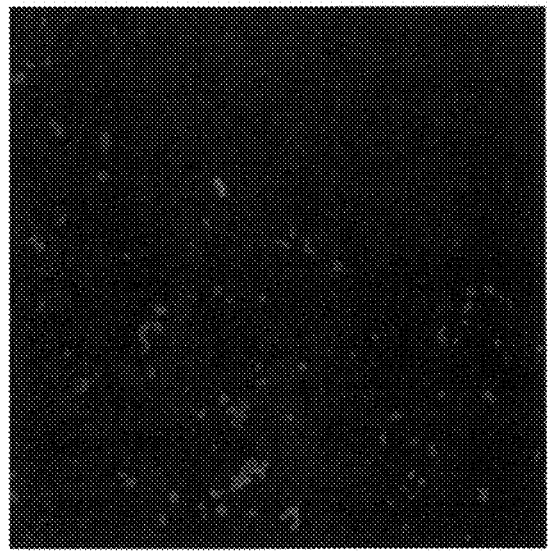

In addition to the undesired labeling of MSSA, the gram-negative species initial dilutions in co-culture interfered with labeling and fluorescence of the previously established gram-positive FCBA. The images of FIGS. 15A and 15B detail two different co-culture plates of *A. baumannii* and *S. aureus* prepped for CLSM with the full gram-positive and gram-negative FCBA protocol. The single difference between FIGS. 15A and 15B is the dilution of the gram-negative primary antibody, whose dilution strength was theorized to contribute to the unwanted labeling effects. The gram-negative primary antibody dilution of the image of FIG. 15A is 1:200 and 1:400 in the image of FIG. 15B.

The procedure for the Gram Positive+New Gram Negative CLSM Assay (on co-cultures) took approximately 5 hours 15 minutes and was performed as follows:
1) 3×5 minute PBS washes;
2) Block with BSA, 30 minutes;
3) Introduce gram-negative 1° [LPS gram-negative anti-goat] 10=1:200, 11=1:400, 60 minutes;
4) 2×5 minutes PBS washes;
5) Introduce gram-negative 2° [Alexa Fluor 568] 1:200, 60 minutes;
6) 2×5 minute PBS washes;
7) Introduce gram-positive 1° [gram-positive LTA] 1:100, 60 minutes;
8) 2×5 minutes PBS washes;
9) Introduce gram-positive 2° [rabbit anti-IgG Fc FITC] 1:50, 60 minutes; and
10) Replace with fresh PBS, ready for confocal.

In testing with such protocol, quantification was performed and the results are as follows:

MSSA+*A. baumannii* co-culture 120×, (15A)
Total gram-positive coverage: 0.904±1.668%
Green threshold: 0.90%
Total gram-negative coverage: 1.65±2.87%
Red threshold: 1.82%
MSSA+*A. baumannii* co-culture 120×, (15B)
Total gram-positive coverage: 0.0621±13.8%
Green threshold: 0.08%
Total gram-negative coverage: 0.0289±2.471%
Red threshold: 2.45%.

Figure 16A:
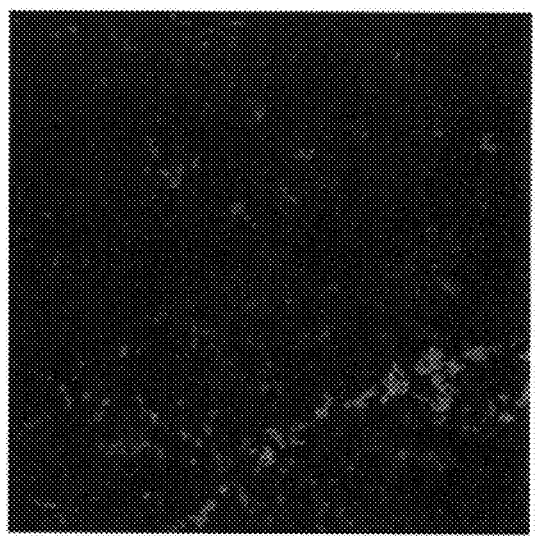
FIGS. 16A and 16B are co-culture study images that were prepared with the same assay protocol as the sample images of FIGS. 15A and 15B except with further modulations in gram-negative dilution factor in accordance with the subject technology.
Figure 16B:
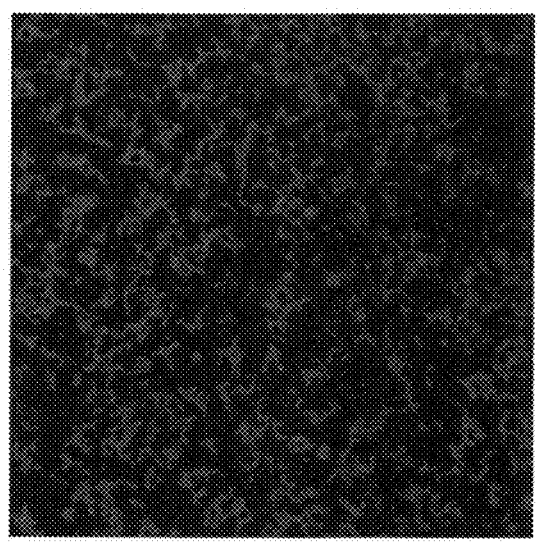

Referring now to FIGS. 16A and 16B, additional co-culture study images are shown that were prepared with the same assay protocol as the sample images of FIGS. 15A and 15B except with further modulations in gram-negative dilution factor. The image of FIG. 16A has a gram-negative primary antibody dilution factor of 1:600. The image of FIG. 15B has a gram-negative primary antibody of 1:1000. Progressive improvements in bleed-through and overlapping fluorescent signals are observed with the weakening of the gram-negative antibody dilution.

In testing with such protocol, quantification was performed and the results are below.

MSSA+*A baumannii* co-culture 120×, (16A)
Total gram-positive coverage: 1.65±0.980%
Green threshold: 1.84%
Total gram-negative coverage: 8.05±0.883%
Red threshold: 8.37%
Overall bacterial coverage: 10.84±1.201%
Overall coverage threshold: 11.12%
MSSA+*A baumannii* co-culture 120×. (16B)
Total gram-positive coverage: 1.725±0.336%
Green threshold: 3.84%
Total gram-negative coverage: 5.57±0.345%
Red threshold: 7.33%
Overall bacterial coverage: 28.76±0.436%
Overall coverage threshold: 28.87%

Investigations were performed with the co-culture experimental model. Because the dilution strength of the gram-negative primary antibody was nearing that of a balanced signal, another modification was implemented and the gram-negative primary dilution factor was kept at 1:1000. In addition, rabbit serum was added to the blocking, PBS washing, and antibody introduction steps. The addition of rabbit serum was implemented in order to block the expression of protein A, an element encountered in gram-positive cell walls theorized to cause the observed cross labeling. Two plates were prepared according to the full assay detailed above, with several modifications—most notably the addition of 20% or 40% rabbit serum to the BSA blocking in FIGS. 17 and 18, respectively. Additionally, 1% rabbit serum PBS was used in all washes and antibody dilutions. Rabbit serum was added to block the fluorescence of Protein A, and in both images no cross talk is observed, with balanced fluorescence from both the green and red channels.

Figure 17:
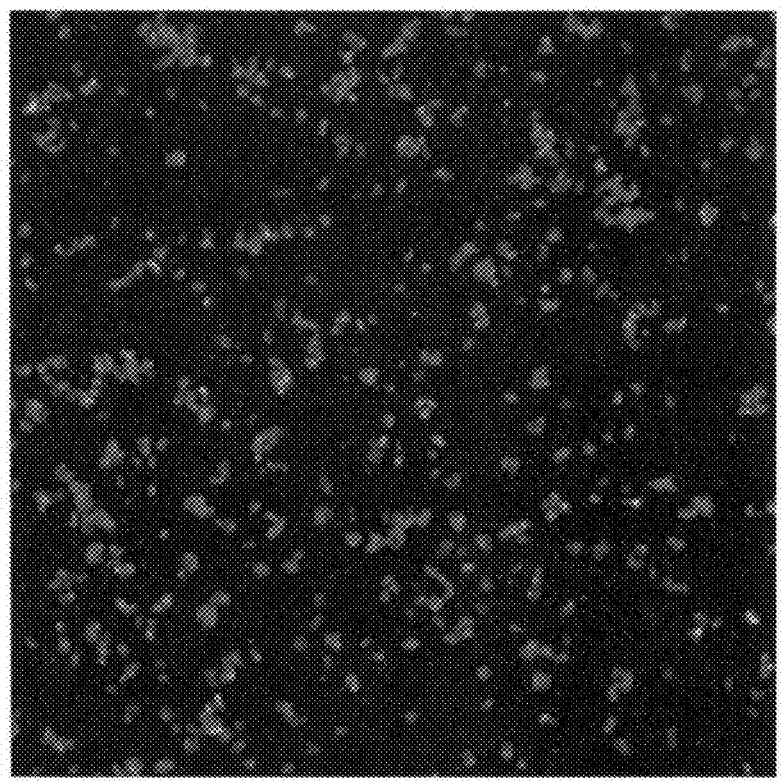
FIG. 17 is an image of a successful co-culture assay with the addition of 20% rabbit serum in accordance with the subject technology.

FIG. 17 is a successful co-culture assay with the addition of 20% rabbit serum. The results of quantification are below.
MSSA+*A baumannii* co-culture+20% RS 120×, (17A)
Total gram-positive coverage: 9.67±0.776%
Green threshold: 9.89%
Total gram-negative coverage: 6.66%±1.62%
Red threshold: 9.46%
Overall bacterial coverage: 14.73±1.12%
Overall coverage threshold: 16.64

Figure 18:
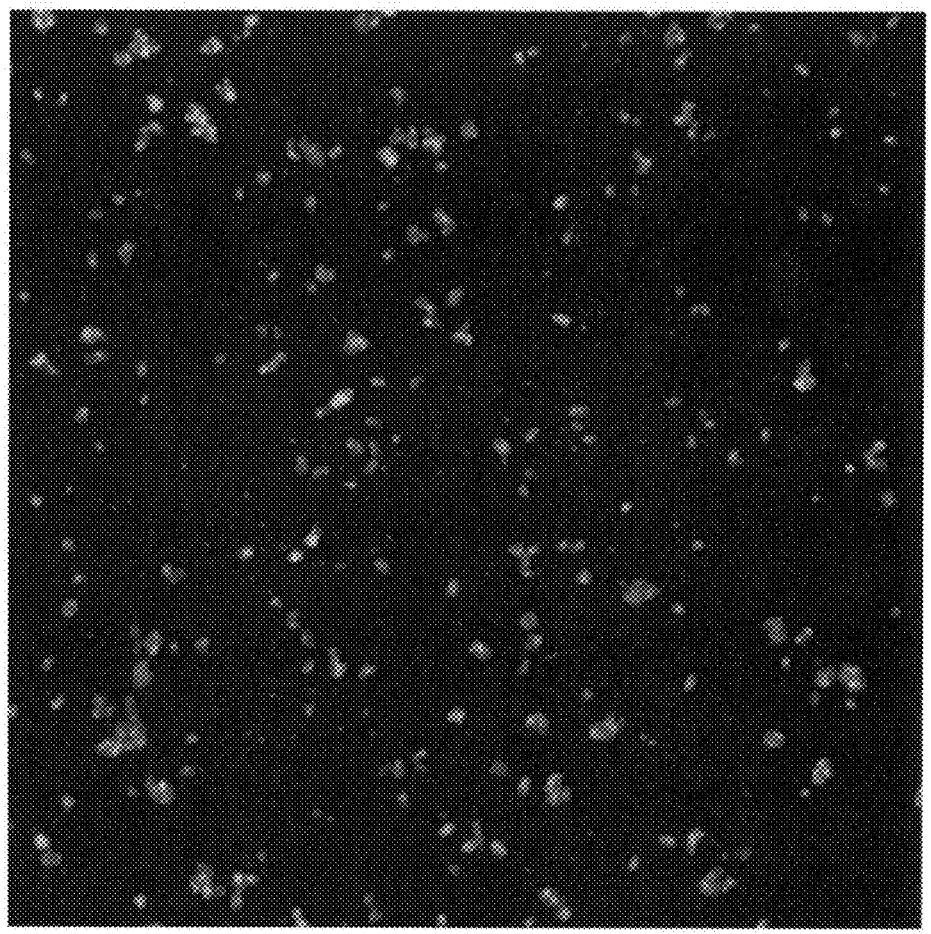
FIG. 18 is an image of a successful co-culture assay with the addition of 20% rabbit serum in accordance with the subject technology.

FIG. 18 is a successful co-culture assay with the addition of 40% rabbit serum. The results of quantification are below.
MSSA+*A baumannii* co-culture+40% RS 120×, (18A)
Total gram-positive coverage: 6.934±1.57%
Green threshold: 7.23%
Total gram-negative coverage: 5.56±1.74%
Red threshold: 8.04%
Overall bacterial coverage: 10.46±1.79%
Overall coverage threshold: 14.01%

Phase 5: Enhancement of Assay with Eukaryotic Culture Model

The developments in proper gram-negative dilution and Rabbit Serum blocking also enabled further experimentation in our laboratory into FCBA staining and CLSM analysis with eukaryotic and bacterial co-cultures. This in parallel eukaryotic/bacterial culture model experimentation, led by Caryn Cobb and Dr. Garcia, provided an in-vitro template for optimizing the now-established co-culture protocol for time and image quality. Eukaryotic cells are clearly observed, with engulfing gram-positive biofilm. Gram-negative presence is also noted. Most notably, this eukaryotic/dual-bacteria co-culture was prepped for CLSM in one hour.

Figure 19:
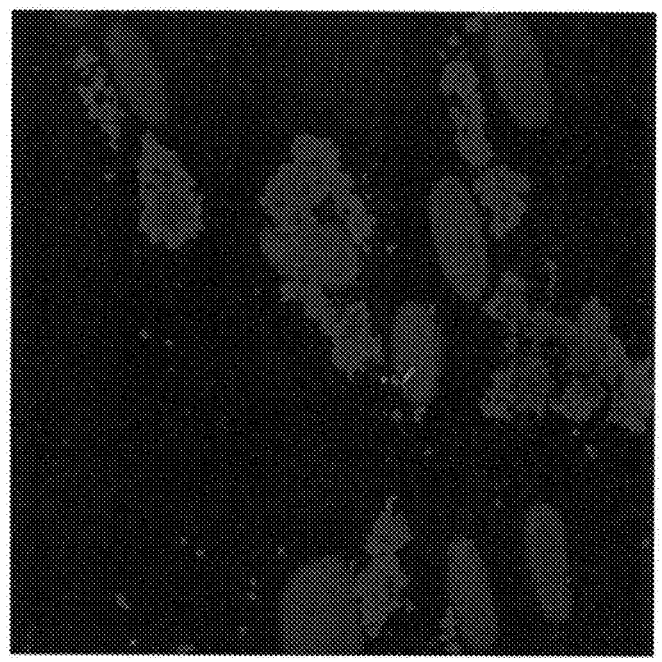
FIG. 19 is an image of an eukaryotic and dual-bacterial species model image in accordance with the subject technology.

FIG. 19 is a eukaryotic and dual-bacterial species model image. In more detail, the particulars of the assay are below.
Gram Positive+Gram Negative CLSM Assay: 45 minutes
1) 3×PBS+1% Rabbit Serum (RS) washes, straight through
2) Block with 50% BSA±50% RS, 15 min
3) Introduce 1° antibody of both gram-positive and gram-negative, 15 minutes
   [gram-positive LTA] 1:100
   [LPS gram-negative anti-goat] 1:1000
4) 3×PBS+1% RS washes
5) Introduce 2° antibody of both gram-positive and gram-negative, 15 minutes
   [rabbit anti-IgG Fc FITC] 1:50
   [Alexa Fluor 568] 1:200
6) Rinse with PBS+1% RS, ready for confocal.
The results of quantification of FIG. 19 are below.

MSSA+*A. baumannii*+Euk (20% RS) 120×: 1 hour protocol (19A)
Gram. Positive Bacteria: 12.54±0.757%
Green Threshold: 12.52%
Gram Negative Bacteria: 0.992±3.166%
Red Threshold: 1.43%
Eukaryotic Cells: 9.629±0.773%
Blue Threshold: 9.75%
Percent Area. Coverage: 18.013±0.643%
Total Threshold: 18.21%

Further experimentation into rabbit serum blocking and replication of clear visualization and characterization was conducted using an eukaryotic/dual-bacteria co-culture model with the results shown in FIG. 20A. The image of FIG. 20A illustrates the results of a blocking step of 50% Rabbit Serum/50% BSA. Once again, clear eukaryotic tissue along with bacterial presence is noted, with a FCBA/CLSM preparation assay time of 1 hour.

Figure 20:
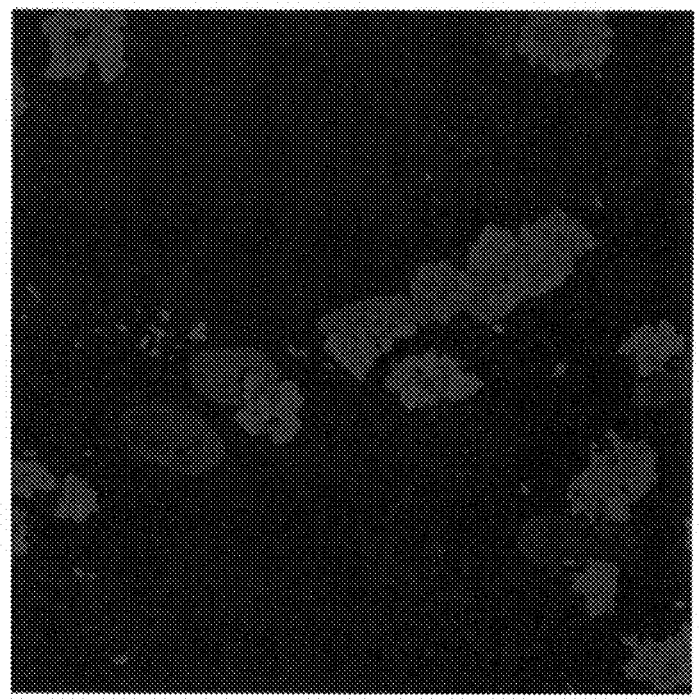
FIG. 20 is an image of eukaryotic and dual-bacterial species assay work with 50% rabbit serum in accordance with the subject technology.

FIG. 20 is an eukaryotic and dual-bacterial species assay work with 50% rabbit serum. In more detail, the particulars of the assay are below.
MSSA+*A. baunannii*+Euk (50% RS) 120×: 1 hour protocol (20A)
Gram Positive Bacteria: 11.52±0.647%
Green Threshold: 11.51%
Gram Negative Bacteria: 0.356±4.116%
Red Threshold: 0.68%
Eukaryotic Cells: 9.53±1.169%
Blue Threshold: 9.57%
Percent Area Coverage: 16.23±0.975%
Total Threshold: 16.31%

Phase 6: Continued Preparation of Explants

Additional work was performed on explants to negate crosstalk between antibodies, refine dilutions, and block undesired background autofluorescence and cross talk. As a result, rapid FCBA labeling of explanted orthopaedic hardware, and subsequent visualization and characterization of potential bacterial adhesion or biofilm formation has been accomplished.

Figure 21A:
FIGS. 21-26 are various CLSM images in accordance with the subject technology.
Figure 21B:
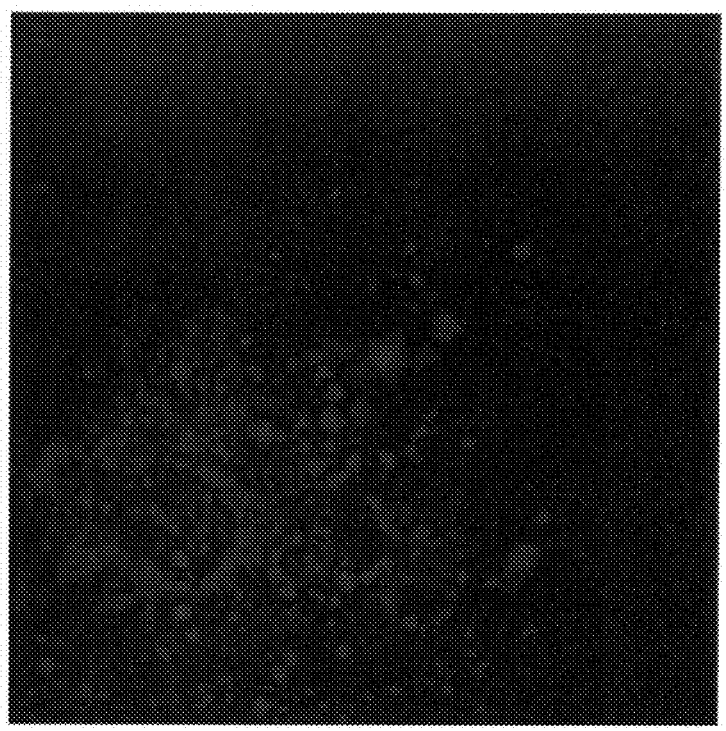
Figure 22:
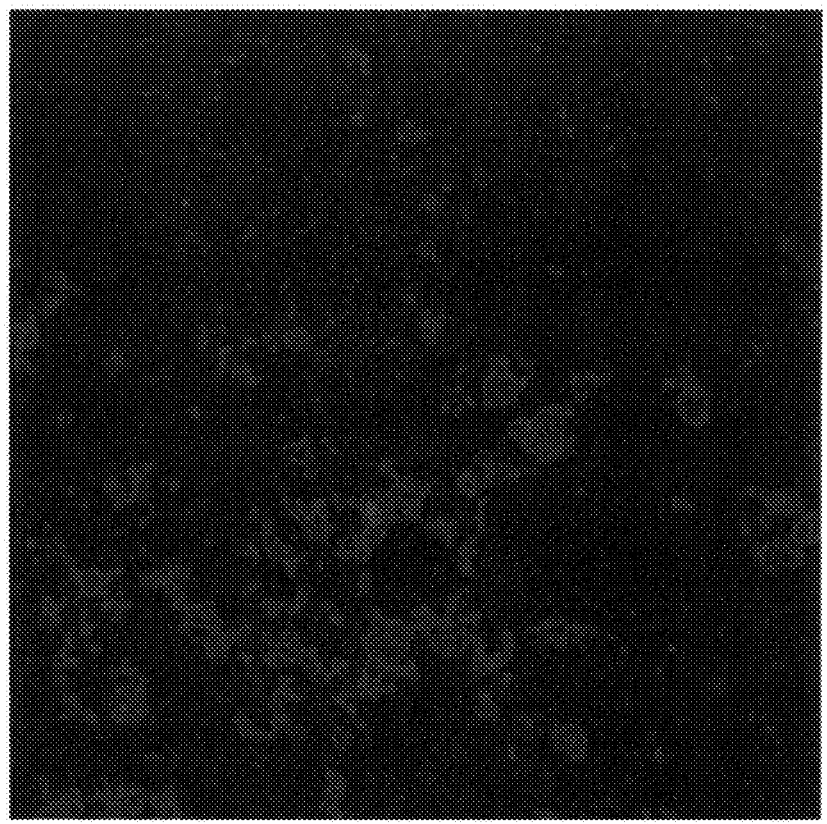

Referring to FIGS. 21A, 21B and 22, the images of FIGS. 21A and 21B detail gram-positive bacterial presence, with thorough eukaryotic tissue noted in 21B. The image of FIG. 22 details definitive gram-negative bacterial presence, interspersed with native tissue adherence. The explants used to create the images of FIGS. 21A, 21B and 22 were prepared according to the extended full gram-positive+gram-negative FCBA assay. The extended explant assay was utilized, in order to validate the preparation protocol on explants (translating from co-cultures) before investigating time optimization.

The full refined assay protocol for the explants for FIG. 21A is below. The Gram Positive+Gram Negative CLSM Assay is approximately 4 hours, 45 minutes.
1) 3×PBS+1% RS washes
2) Block with BSA+RS, 30 minutes
3) Introduce gram-positive 1° [gram-positive LTA] 1:100, 60 minutes
4) 2×PBS washes+1% RS washes
5) Introduce gram-positive 2° [rabbit anti-IgG Fc FITC] 1:50, 60 minutes
6) 2×PBS+1% RS washes
7) Introduce gram-negative 1° [LPS gram-negative anti-goat] 1:1000, 60 minutes
8) 2×PBS+1% RS washes
9) Introduce gram-negative 2° [Alexa Fluor 568] 1:200, 60 minutes 10) 2×PBS+1% RS washes, ready for CLM [0165] The results of quantification are below.

Screw Head 120× (21B)
Gram Positive Bacteria: 4.95±0.989%
Green Threshold: 5.19%
Eukaryotic Cells: 0.581±1023%
Blue Threshold: 0.65%
Percent Area Coverage: 6.21±1.17%
Total Threshold: 6.49%
Screw Head, Full Assay 120× (21C)
Gram Positive Bacteria: 1.98±1.22%
Green Threshold: 2.40%
Eukaryotic Cells: 0.895±0.364%
Blue Threshold: 1.09%
Percent Area Coverage: 3.79±0.722%
Total Threshold: 4.30%

Referring now to FIG. 22, FIG. 22 illustrates a confocal image from a screw head prepped with full assay with gram-negative species. The results of the quantification of this screw head are as follows.

Screw Head, Full Assay 120× (22B)
Gram Negative Bacteria: 2.74±1.19%
Red Threshold: 3.48%
Eukaryotic Cells: 9.63±0.977%
Blue Threshold: 10.09%
Percent Area Coverage: 6.27±0.77%
Total Threshold: 6.86%

Figure 23:
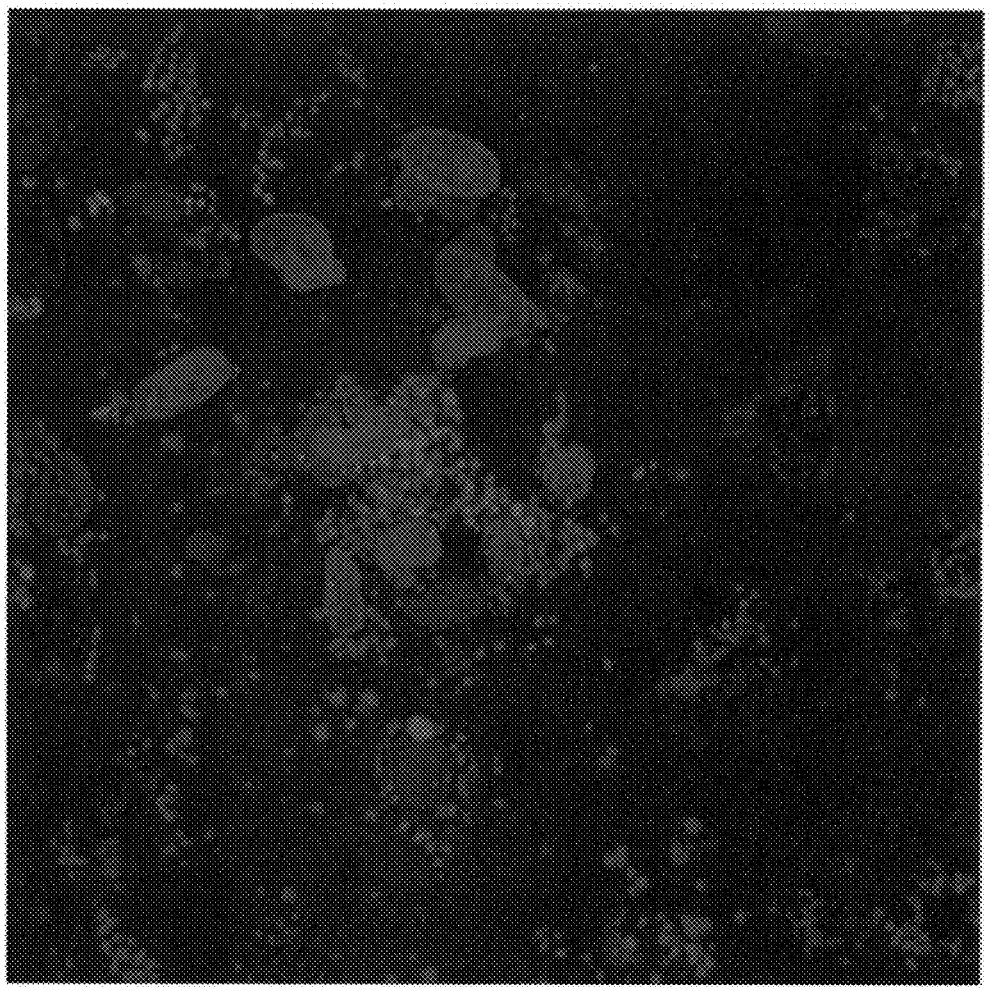

Referring now to FIG. 23, a fragment of polymethyl methacrylate bone cement, was prepared according to a gram-positive explant preparation protocol to generate the image shown therein. The clear CLSM resultant image of gram-positive cocci and biofilm formation in the image of FIG. 23 serves as a standard for clear visualization and characterization of bacterial biofilm adhesion on explanted hardware. Clear eukaryotic tissue presence is noted engulfed among gram-positive colonies.

Phase 7: Implementation and Refinement of Rapid Preparation Assay

Quantification:
Screw Head 120× (23B):
Gram Positive Bacteria: of 6.49±1.67%
Green Threshold: 7.10%
Eukaryotic Cells: 1.25±1.15%
Blue Threshold: 12.62%
Percent Area Coverage: 20.05±1.11%
Total Threshold: 20.38%

With clear visualization accomplished on a number of explants via the extended assay, experimentation began on implementation of a 45-minute CLSM preparation protocol. The below representative image of FIG. 24 details the results from implementation of the 45-minute rapid assay on explants. The image of FIG. 24 was generated from a piece of poly(methyl) methacrylate (A) that was prepared according to the 45 minute assay. The image of FIG. 24 displays native eukaryotic tissue with a lack of definable bacterial colonization.

Figure 24:

The quantification of the explant CLSM under the 45-minute protocol of FIG. 24 is as follows.

PMMA bone cement rapid assay 120× (24B):
Gram Positive Bacteria: 0.285±0.508%
Green Threshold: 0.46%
Gram Negative Bacteria: 0.381±0.626%
Red Threshold: 0.57%
Eukaryotic Cells: 1.248±3.63%
Blue Threshold: 1.33%
Percent Area Coverage: 3.36±0.867%
Total Threshold: 3.72%

A Gram Positive+Gram Negative CLSM Assay for 45 minutes is also as follows.

Figure 25:

1) 3×PBS+1% Rabbit Serum (RS) washes, straight through
2) Block with 50% BSA+50% RS, 15 minutes
3) Introduce 1° antibody of both gram-positive and gram-negative, 15 minutes—Gram positive: [gram-positive LTA] 1:100
Gram negative: [LPS gram-negative anti-goat] 1:1000
4) 3×PBS+1% RS washes, straight through
5) Introduce 2° antibody of both gram-positive and gram-negative, 15 minutes—Gram positive: [rabbit anti-IgG Fc FIX] 1:50
Gram negative: [Alexa Fluor 568] 1:200
6) Rinse with PBS+1% RS, ready for confocal.
7) Referring now to FIG. 25, an image generated from a screw head prepared with a rapid 45-minute full assay shows definitive gram-negative colonization. Although a large streak of red through the lower half of the image of FIG. 25 demonstrates autofluorescnce and background of the screw head's surface, the upper left quadrant details red signals consistent with gram-negative cocci morphology.

The quantification of the explant CLSM using the 45-min protocol in FIG. 25 is as follows.

Screw Head Rapid Assay 120× (25B):
Gram Positive Bacteria: 0.028±0.6424%
Green Threshold: 0.18%
Gram Negative Bacteria: 3.185±0.575%
Red Threshold: 5.44%
Eukaryotic Cells: 3.196±1.023%
Blue Threshold: 3.21%
Percent Area Coverage: 4.58±0.522%
Total Threshold: 6.37%

Figure 26:
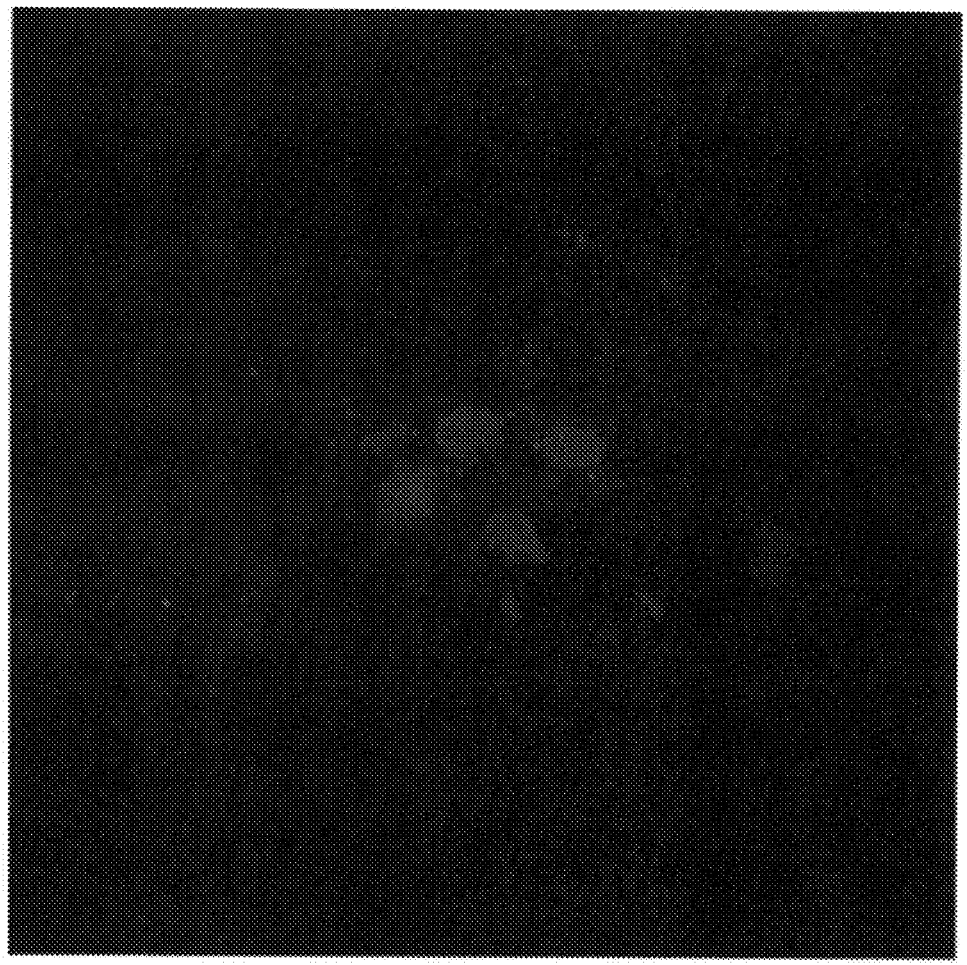

Referring to FIG. 26, another screw head was also prepared with the 45-minute protocol and the resulting CFSL image is shown. The center of the image of FIG. 26 details eukaryotic tissue, with extremely limited coverage of both gram-positive and gram-negative cocci also present.

The quantification for this screw head using the explant CLSM, 45-minute protocol is as follows.

Screw Head Rapid Assay 120× (26B):
Gram Positive Bacteria: 0.451±1.364%
Green Threshold: 0.59%
Gram Negative Bacteria: 1.167±1.1003%
Red Threshold: 1.63%
Eukaryotic Cells: 1.465±2.309%
Blue Threshold: 1.51%
Percent Area Coverage: 2.843±0.89%
Total Threshold: 3.03%

As can be understood by those of ordinary skill in the art based upon review of the above, it has been established that by utilizing the technology of FCBAs and CLSM, both bacterial control plates and explants can be effectively visualized and analyzed for bacterial biofilm growth. The development of this novel assay methodology can be traced through the results of bacterial plate experimentation and explant preparation through the themes of both quantification and total assay time. Quantification of notable results indicates the level with which effective labeling has occurred, and enables overall insight into the evolution of the novel assay's efficacy.

Quantification and Critical Analysis

As seen in the Results section, notable images have been quantified using ImageJ software. The image is separated into Green, Red, and Blue channels, indicating respective presence of gram-positive, gram-negative, and eukaryotic cells. Within each channel, a saturation threshold is determined by modulating the saturation of each color, in order to isolate completely labeled and identifiable objects and mitigate background and autofluorescence. Once the threshold is chosen, the relative areas of coverage for each color channel is determined, along with standard deviation. Over the course of the assay development, the quantification of notable images indicates the improvements in FCBA labeling methodology. In the images of FIGS. 8A and 8B, the MSSA control contains bacterial coverage of 20.88±0.582% while the *A. baumannii* control exhibits coverage of 39.268±0.462%. Intuitively, these bacterial controls demonstrate the largest observed bacterial coverage of any images. Additionally, their small standard deviations indicate consistent signal strength throughout the labeled objects, pointing towards effective labeling.

With the initiation of explant processing, quantification enabled critical analysis of bacterial coverage calculations and staining efficacy is possible. The sample known to be infected with MSSA (FIG. 9) demonstrated abundant eukaryotic coverage and small green cocci consistent with gram-positive colonization. The image of FIG. 10B, with bacterial coverage of 2.32±1.132%, and the image of FIG. 10C, with coverage of 2.134±1.312%, both indicate that while bacteria is certainly present, determination of the saturation threshold of green-labeled objects was difficult because of a range of green signals. Similar findings are exhibited in FIGS. 11A and 11B, in which a range of green-strength fluorescent signals, as well as a wide collection of artifact size, translates to some ambiguity in characterization. Although these explants were found to be infected with a gram-positive species, the quantification of their bacterial coverage (and standard deviation) indicated potential improvement by protocol revision. The images of FIGS. 12A and 12B also demonstrate this finding, in which total gram positive coverage was found to be 0.378±3.889% (B) and 0.399±4.235% (C), and gram-negative coverage was found to be 0.048±27.067% (B) and 0.094±16.532% (C).

With quantification results and ambiguity in bacterial characterization serving as impetus for protocol revision and refinement, focus was directed back towards bacterial plate experimentation. Troubleshooting in these phases was largely enabled by quantification. The images of FIGS. 15A and 15B (of MSSA and *A. baumannii* co-cultures) detail the initial stages of troubleshooting the phenomena of bleedthrough between the gram-positive and gram-negative antibodies. The gram-positive bacterial coverage shown in FIGS. 15A and 15B (0.904±1.668% and 0.0621±13.8%, respectively) indicate that a great deal of bleedthrough is occurring, preventing a balanced and uniformly consistent gram-positive stain. Visual analysis clearly shows that the gram-negative bacterial coverage is interfering with a balanced simultaneous red and green characterization.

An appreciable degree of assay labeling improvement is demonstrated in FIGS. 16A and 16B. Visual inspection shows that while overlap is still occurring (manifested by cocci that appear to fluoresce as orange or yellow objects) individual red and green bacterial species can be differentiated. Similarly, quantification of these images validates the improvement that the assay modulation (decreasing the strength of the gram-negative primary antibody) yielded. Gram-positive and grain-negative coverage in the image of FIG. 16A was found to be 1.65±0.980% and 8.05*0.883% respectively. These relatively smaller standard deviations indicate that more consistent detection of balanced signal strength is achieved, and the overall percent abundance of each species is more balanced. Further improvement is demonstrated in the image of FIG. 16B, in which gram-positive coverage was observed at 1.725±0.336% and gram-negative coverage was observed at 5.57±0.345%. While a large degree of overlap in fluorescent signals is noted, the standard deviations of both species indicate a more consistent signal detection threshold. Additionally, the relative abundances of the two species are approaching one another as the overall antibody staining becomes more balanced. Finally, the overall bacterial coverage (28.76±0.436%) is approaching the coverage previously observed in the initial individual bacterial plates (FIG. 8).

Successful gram-positive and gram-negative culture and labeling was accomplished in FIGS. 17 and 18. Because the aforementioned fluorescence signals of image 16 were approaching proper balance, the gram-negative primary antibody dilution was maintained at 1:1000. Rabbit serum was added to the blocking, PBS washing, and antibody introduction steps. This was implemented in order to block the expression of protein A, an element encountered in gram-positive cell walls theorized to cause the observed cross labeling and fluorescence bleedthrough.

In FIG. 17, gram-positive coverage was quantified to be 9.67±0.776 and gram-negative 6.66%±1.62%. This indicates a much more effective and balanced preparation protocol. Similarly, FIG. 18 exhibits gram-positive and gram-negative coverage of 6.934±1.57% and 5.56±1.74% respectively. Once again, these quantifications indicate balanced total abundance and fluorescent signals between both species, as well as consistent fluorescence thresholds within each gram-labeling scheme. No concerning overlap is observed, reinforcing the strength of the implemented assay refinements.

With the refinements from bacterial culture studies, explant CLSM preparation was reinitiated with a full gram-positive gram-negative detection assay. As shown in the image of FIG. 21B, resulting from full assay prep of a screw head, clear gram-positive growth is demonstrated. Once again, gram-positive bacterial coverage was quantified at 4.95±0.989%, indicating consistently-labeled gram-positive objects despite the addition of the gram-negative labeling. The inverse result was noted in the image of FIG. 22B, in which gram-negative bacterial surface coverage (surrounding eukaryotic cells) is quantified at 2.74±1.19%, with no interference of gram-positive fluorescence.

Although it was not prepared for confocal according to the full assay, the explant (e.g., bone cement fragment) used to generate the image of FIG. 23 provided an image that serves as the exemplary image of incredibly clear visualization, characterization, and quantification. The image, detailing the surface of PMMA bone cement, indicates a gram-positive surface load of 6.49±1.67% surrounding native tissue (20.05±1.11%.). These relatively low standard deviations indicate consistent fluorescent signal thresholds and effective labeling. This image of clear gram-positive coccal morphology is the standard to which clear visualization and characterization of explants processed through the CLSM assay is held.

With a number of full-assay explants prepared and analyzed, experimentation was conducted on implementation of a 45-minute CLSM preparation assay. The image of FIG. 24B details the resultant image of a polymethyl methyacrylate bone cement fragment prepared for CLSM according to the 45-minute protocol. Gram-positive bacteria coverage is not indicated, with surface coverage 0.285±0.508%. Similarly, gram-negative presence (surface coverage 0.381±0.626%) is also not indicated. Although slight amounts of background are noted, the 45-minute protocol (and subsequent quantification) indicate that no bacterial species are present on the explant.

In contrast, the image of FIG. 25B details definitive gram-negative adherence, with surface area 3.185±0.575%. A small standard deviation indicates that, as desired, consistency and balance in red saturation threshold is achieved. Additionally, quantification allows for the mitigation of background and autofluorescence, as demonstrated by the red streak across the image. Because the red saturation threshold lies above the strength of the autofluorescent streak, it is not included in the bacterial surface area calculations. FIG. 26 is an image generated from another screw prepared according to the 45-minute assay. While clear eukaryotic presence is noted along with definitive gram-negative fluorescence, gram-negative area was calculated at 1.167±1.1003%. While FIGS. 24, 25, and 26 (emblematic of imaging results from the 45-minute assay) exhibit a range of quantification findings, these figures demonstrate that explants can effectively be imaged for gram-positive and gram-negative growth in a rapid time interval.

Total Assay Preparation Time and Critical Analysis

In addition to the theme of quantification results, total assay preparation time provides an integral glimpse at the increasing clinical relevance of the assay throughout its development and refinement. FIGS. 19 and 20 detail two images in which MSSA and *A. baumannii* are cultured with eukaryotic cells and prepared for CLSM. Both images of FIGS. 19 and 20 were prepared in one hour. These investigations aided significantly in the ability to decrease the amount of time required to prepare explants for CLSM imaging and analysis. Explants to generate the images of FIGS. 24, 25, and 26 were all prepared and ready for confocal analysis within 45 minutes.

The subject technology allows accurately and rapidly visualizing, characterizing, and quantifying gram-positive and/or gram-negative biofilm foundation on explants closely within the time of removal. Through the use of fluorescent-conjugated antibodies and confocal laser scanning microscopy, the subject technology has developed a clinically relevant rapid detection assay capable of visualizing and quantifying bacterial colonization and biofilm formation in less than one hour.

Within the clinical landscape of infection detection, diagnosis, and treatment, the subject technology provides much improvement. Existing clinically employed methodologies for the detection of microbial presence on orthopaedic implants are still dependent upon successful culture of bacteria from tissue surrounding the implant. These methods are prone to providing false-negative results for slow growing bacteria like *Propionibacterium acnes*, which may additionally take many days to appear in culture. Another benefit of rethinking infection detection is represented in the cost of current microbiological infection testing techniques. Bacterial culturing and isolation, PCR, and other molecular testing costs are relatively expensive, ranging from $100 to $300 with a wide variety among investigations. Based on materials and methods as noted above, an explant specimen set can be prepared and analyzed using our FCBA and CLSM methodology for under $20 or even less.

For the clinical implementation of the rapid detection assay to become a reality, much more investigation is required. Additional bacterial control investigations of varying gram-positive and gram-negative species in the CLSM preparation assay would inform a wider knowledge base of specific bacterial colonization patterns and morphologies. The subject technology includes processing and characterization of explants to build a substantial database with which further assay refinement and clinical outcomes comparisons can be drawn as well as adapting the assay to the particular procedure, explants or sample type, and known trends for the particular circumstances. Additionally, pre-conjugated antibodies can further reduce assay time and increase antibody-labeling specificity for specific bacterial types.

The subject technology provides an accurate and rapid detection assay to provide surgeons with an extremely valuable tool for determining a course of action while the patient is still on the operating table. The subject technology can be vital in improving orthopaedic interventions, expediting infection diagnosis, and refining treatment that will greatly improve patient outcome.

In one embodiment, the subject technology acquires an explants, tissue sample, portion of implant or the like that is placed within a section of a microplate and ELISA agents described in the methods are washed over the sample in succession using the dispensing function of a microplate reader with or without additional manual rinsing steps. A rocker may be utilized to increase the ease and effectiveness of the washing or other steps. The FlexStation 3 Multi-Mode Microplate Reader by Molecular Devices Inc. is an example of a plate reader which can accommodate one multi-well plate for the labeling agents and another plate to hold the implant or tissue sample to be labeled.

In such a case the assay would consist of a kit which includes prepackaged reagents for labeling a group of common pathogenic microbes in a traditional microplate arrangement. A separate custom designed tray for holding the explant or tissue sample can also be used. The reagents would be used to label the explant or sample with fluorophores or chromophores or luminescent molecules for evaluation. An advantage of using the microplate architecture for automation of the methods described is that multi-mode plate reading equipment is readily available and qualified for analysis of bacteria and human tissue. Software routines can be easily written for standard plate readers to automate the assay methods described and confirm the presence of pathogenic infections during a surgical procedure. This enables the doctors to work up a targeted antibiotic treatment and make decisions as to whether it is appropriate to immediately replace the removed implant with a new implant or whether more time should be given for an infection to clear before implanting a new device.

Figure 27:
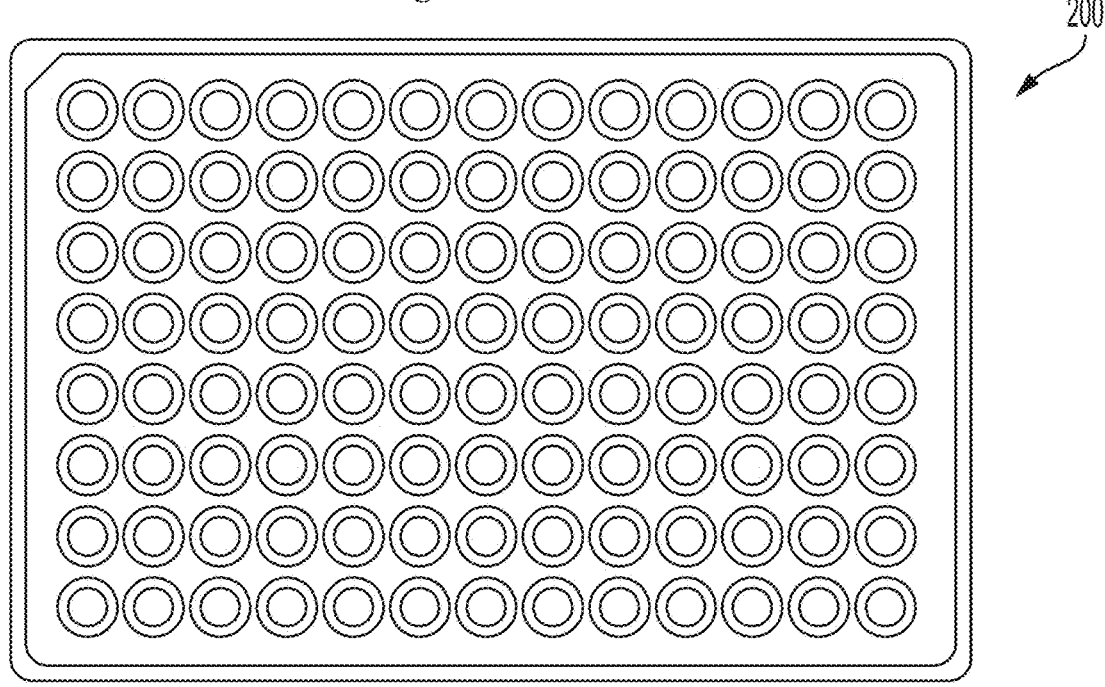
FIG. 27, a schematic top view of a standard microplate 200 with pre-packaged reagents for automatic dispensing in accordance with the subject technology is shown. The microplate 200 may include reagents for any method contemplated here.
Figure 28:
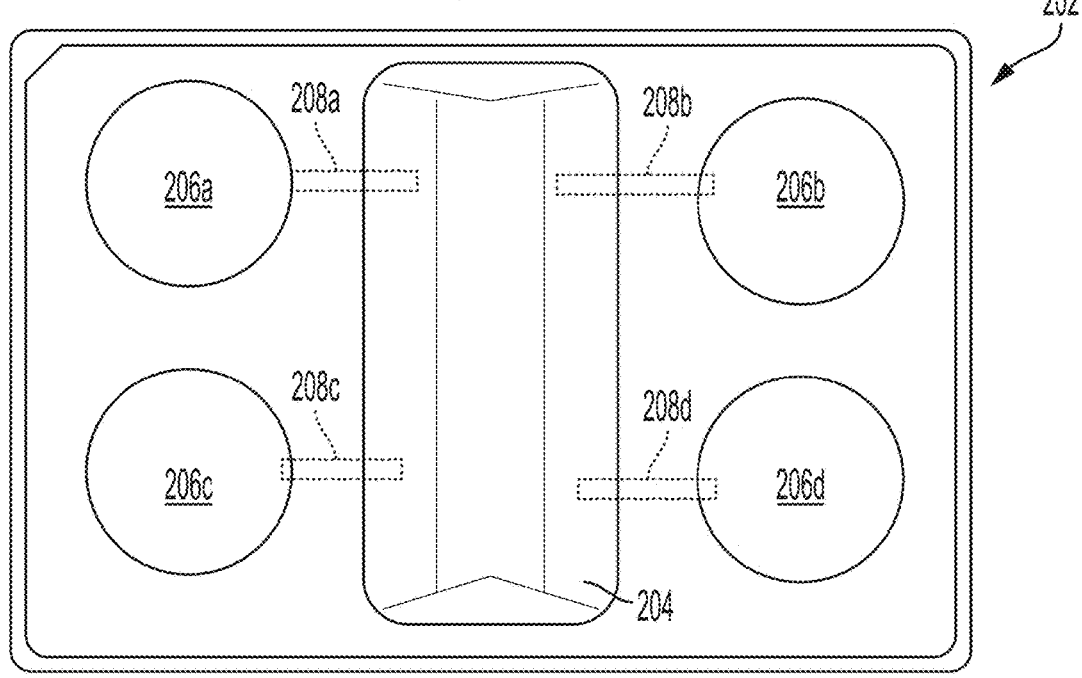
FIG. 28 is a schematic top view of a custom plate as part of an explant assay kit in accordance with the subject technology.
Figure 29:
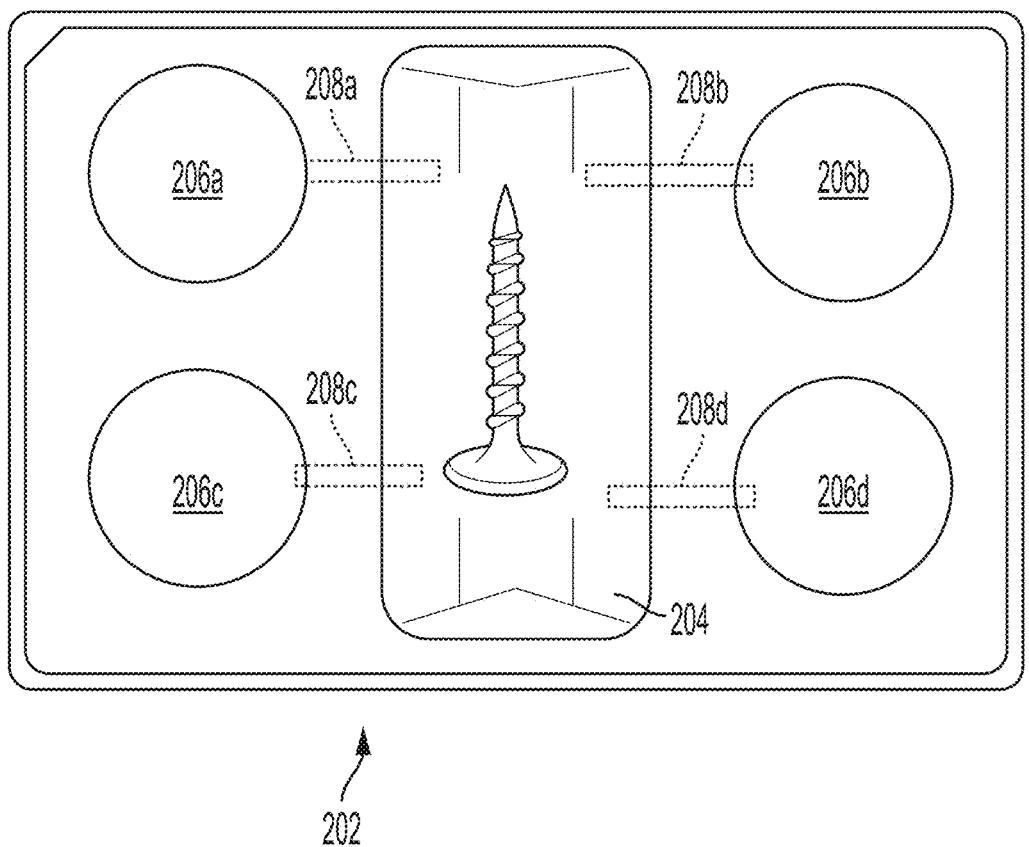
FIG. 29 is a schematic top view of a custom plate as part of an explant assay kit with an explants in place in accordance with the subject technology.

Referring now to FIG. 27, a schematic top view of a standard microplate 200 with pre-packaged reagents for automatic dispensing in accordance with the subject technology is shown. The microplate 200 may include reagents for any method contemplated here. FIGS. 28 and 29 are schematic top views of a custom plate 202 having a center well 204 for holding a sample (e.g., screw, bone cement, tissue scraping etc.). The center well 204 is in fluid communication with four round wells 206a-d. The center well 204 is elevated and sloped to allow drainage of reagents in the four surrounding wells 206a-d via drainage channels 208a-d. FIG. 29 shows an exemplary placement of a screw sample 210 in the custom plate 202.

Figure 30:
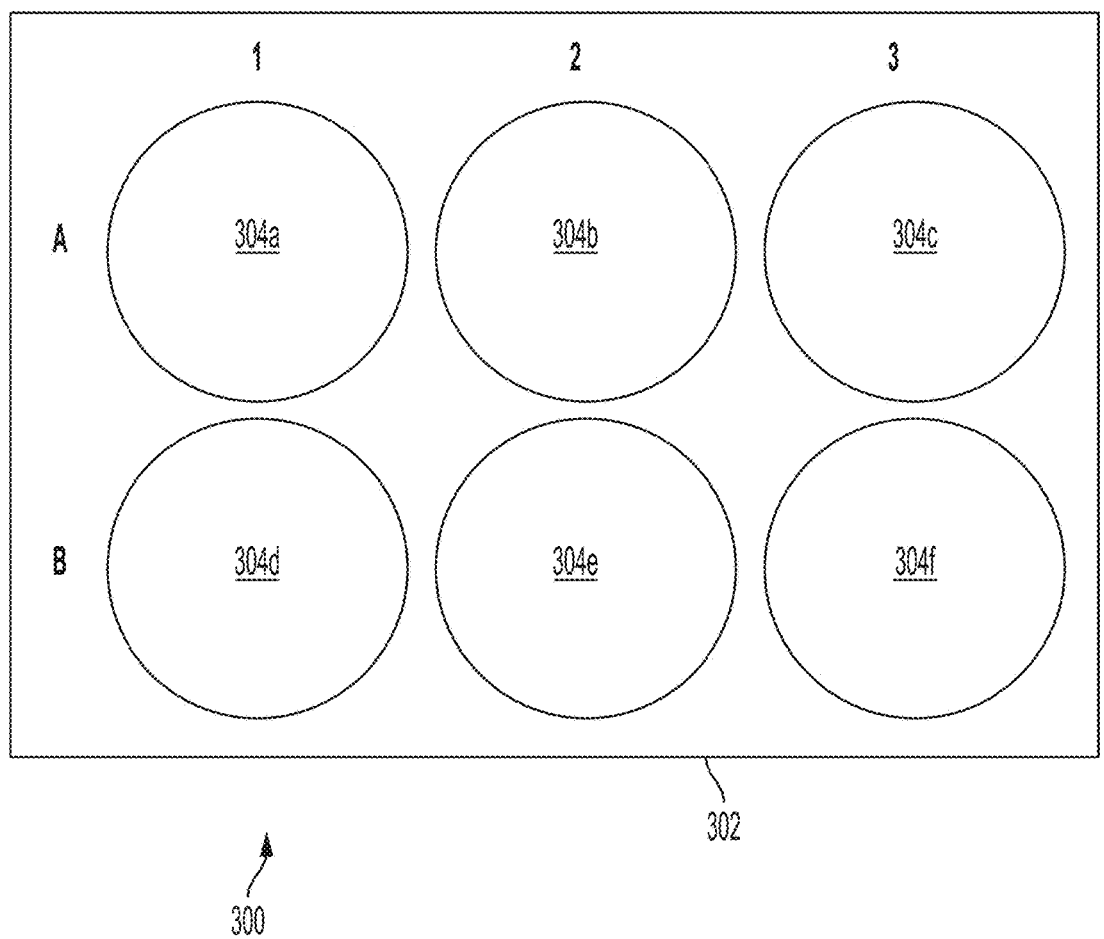
FIG. 30 shows a kit 300 for rapid visualization assay, designed for small solid materials and labels for eukaryotic cells in the form of the nuclear stain DAPI, Gram Positive Cells via FITC, and Gram Negative Cells in the form of AlexaFluor568.

Referring now to FIG. 30, a kit 300 for rapid visualization assay is shown. The kit 300 is designed for small solid materials and labels for eukaryotic cells in the form of the nuclear stain DAPI, Gram Positive Cells via FITC, and Gram Negative Cells in the form of AlexaFluor568. A kit for direct visualization of biofilms at multiple stages of development is also contemplated hereby. Fungal pathogens can also be visualized. Labels can be customized to any number of colors to suit the number of probes utilized. Preferably, the kit 300 is ready to go or configured with simple to mix working solutions.

The kit 300 includes at least one solid black or black/clear bottom well plate 302 for holding the working solutions. In one embodiment, the well plate 302 has six wells 304a-f. The kit 300 provides a simple, step by step submersion/and incubation procedure to be conducted at room temperature. For example, well 304A contains a rinse buffer that will remove any fixing agent or blood. Well 304b contains a cocktail of blocking buffers designed to minimize background and non-specific binding of the antibodies. Well 304c contains conjugated antibodies in buffer or lyophilized. Well 304d contains a buffer rinse with DAPI. Wells 304e and 304f contain additional buffer. Kits can be adjusted for liquid samples by providing glass slides and/or additional markers for biofilms.

Figure 32:
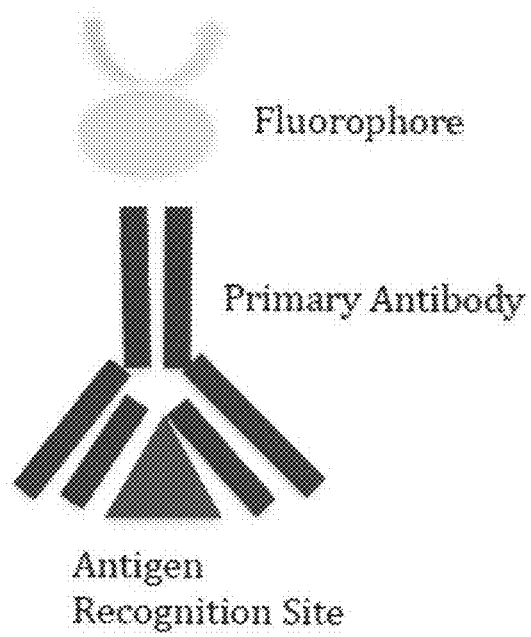
FIG. 32 is an image depicting antibody staining with fluorescent-conjugated antibodies. In this direct assay, the fluorophore is conjugated to a single antibody that is attached to the antigen, LTA site, on the gram positive bacteria.
Figure 31:
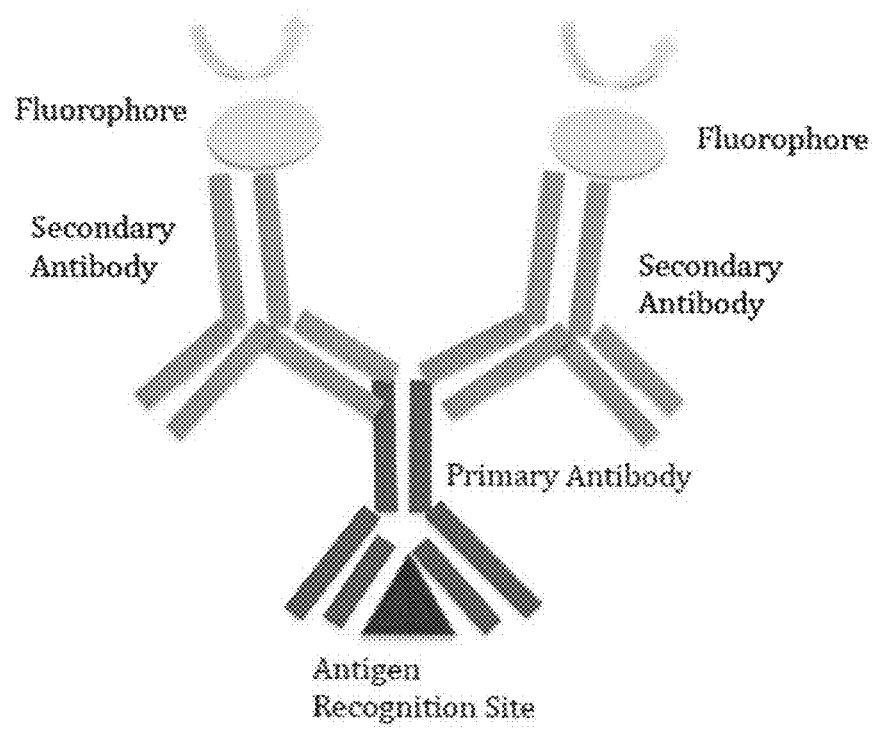
FIG. 31 is an image depicting antibody staining with fluorescent-conjugated antibodies.

Referring to FIGS. 31 and 32, images depicting antibody staining are shown. Antibody staining with fluorescent-conjugated antibodies helps to identify the bacteria present. In FIG. 31, the primary antibody binds to the antigen recognition site, which is located on the bacteria (i.e., LTA or LPS). The conjugated secondary antibody, which is conjugated to the fluorophore, binds to the variable region on the primary antibody. The antibodies are capable of penetrating biofilm, which is evident by the fact that the bacteria in biofilm fluoresces and is visible on an orthopaedic explants under CLSM.

The process of antibody conjugation can be accomplished through a direct or an indirect assay. In a direct assay, the fluorophore is conjugated to a single antibody that is attached to the antigen, LTA site, on the gram positive bacteria as shown in FIG. 32. In an indirect assay, the fluorophore is conjugated to the secondary antibody, which binds to the primary antibody after it is bound to the antigen recognition site on the bacteria as shown in FIG. 31, which is an indirect assay with multiple secondary antibodies. An indirect assay can have an amplified signal due to more than one secondary antibody attaching to the primary antibody. However, this phenomenon can be overcome by diluting the secondary solution in order to avoid excessive background that could result from enhanced amplification.

It is also envisioned that the assay can be conducted with primary antibody omission. Primary antibody omission is when the primary antibody is left out to ensure no nonspecific binding of the secondary antibody. As a result, the determination of visualization problems is aided. Further, the time that the samples are exposed to antibodies could be reduced to further speed up the assay. Another improvement is to tune the assay to particular applications or use different sample types (e.g., tissue or synoval fluid) to detection infection and colonization in vivo. Synovial fluid and peri-implant tissues are recommended for microbial diagnosis of orthopaedic implant-associated infections. Still further, nanoparticle conjugated antibodies to visualize where an infection lies without having to remove the implant can be imaged by using an X-ray or like device.

In another embodiment, the following protocol results in an approximately 30 minute procedure to ready a sample (e.g., an explant) for imaging on a CLSM. The first step is to gently rinse the explant three times with a solution of phosphate buffered saline containing 25% rabbit serum. Following the rinse step, block the sample with a pre-made solution of bovine serum albumin and rabbit serum at a ratio of 1:1. The sample should be left in the solution for approximately 15-20 minutes, preferably on a rocker at 50 revolutions per minute at room temperature. After rocking, the sample is removed from the blocking solution and a cocktail of conjugated gram positive and gram negative antibodies is added. In one embodiment, the gram positive antibody ratio is 1:200 and the gram negative antibody ration is 1:750. The antibody solution is preferably at 37 degrees Celsius. The antibody solution can be warmed in a warm water bath prior to use. The explant is incubated in the dark for approximately 15 minutes. After incubation, the explants can be stored in phosphate buffered saline at 4 degrees Celsius for an extended period of time (e.g., a week) or imaged immediately.

It would be appreciated by those skilled in the art that various changes and modifications can be made to the illustrated embodiments without departing from the spirit of the present technology. All such modifications and changes are intended to be within the scope of the present technology.

What is claimed:

1. A method for visualizing and quantifying bacterial colonization and biofilm formation on an explant comprising the steps of:
   1) washing the explant at least once with a first solution of phosphate-buffered saline (PBS) Bovine Serum Albumin (BSA) Blocking Buffer, and 1% Rabbit Serum (RS) straight through;
   2) applying 1° (primary) antibodies both specific for gram-positive bacteria and specific for gram-negative bacteria for a first period of time;
   3) washing the explant at least once with PBS, BSA Blocking Buffer and 1% RS straight through;
   4) introducing 2° (secondary) antibody specific for 1° (primary) antibodies specific for both gram-positive bacteria and gram-negative bacteria and conjugated to a fluorophore for a second period of time;
   5) rinsing with PBS, BSA Blocking Buffer and 1% RS; and
   6) viewing the explants with confocal laser scanning microscopy (CLSM) for gram-positive and gram-negative adherence.

2. The method of claim 1, wherein
   the at least once wash of steps 1) and 3) is three times each; and
   the first and second periods of time are approximately 15 minutes each.

3. The method of claim 1, further comprising the step of wrapping tin foil around the explants throughout steps (1)-(5) to prevent light-induced damage and photobleaching.

4. The method of claim 1, further comprising the step of multiple iterations of antibody dilution testing in bacterial plates to ensure balanced fluorescence between antibody types of gram positive and gram negative primary and secondary to minimize bleedthrough.

5. The method of claim 1, further comprising the step placing the explant on a rocker for a gentle washing effect at 30 rpm.

6. The method of claim 1, further comprising the step arranging views from the CLSM into a three-dimensional rendering of a surface of the explants.

7. A method for visualizing and quantifying bacterial colonization and biofilm formation on an explant comprising the steps of:
   1) washing the explant at least once with a first solution of phosphate-buffered saline (PBS), Bovine Serum Albumin (BSA) Blocking Buffer and 1% Rabbit Serum (RS) straight through;
   2) blocking with a second solution of 50% Bovine Serum Albumin (BSA) and 50% RS for a first period of time;

3) introducing 1° (primary) antibodies specific for both gram-positive bacteria and specific for gram-negative bacteria for a second period of time;
4) washing the explant at least once with PBS, BSA Blocking Buffer and 1% RS straight through;
5) introducing 2° (secondary) antibody specific for 1° (primary) antibodies specific for both gram-positive bacteria and gram-negative bacteria and conjugated to a fluorophore for a third period of time;
6) rinsing with PBS Blocking Buffer and 1% RS; and
7) viewing the explants with confocal laser scanning microscopy for gram-positive and gram-negative adherence.

8. The method of claim 7, wherein
the at least once wash of steps 1) and 3) is three times each; and
the first, second and third periods of time are approximately 15 minutes each.

9. A method for visualizing and quantifying bacterial colonization and biofilm formation on an explant comprising the steps of:
1) washing the explant at least once with a first solution of phosphate-buffered saline (PBS), Bovine Serum Albumin (BSA) Blocking Buffer and 1% Rabbit Serum (RS) straight through;
2) applying 1° (primary) conjugated antibodies both specific for gram-positive bacteria and specific for gram-negative bacteria for a first period of time;
3) washing the explant at least once with PBS, BSA Blocking Buffer and 1% RS straight through;
4) viewing the explants with confocal laser scanning microscopy (CLSM) for gram-positive and gram-negative adherence.

* * * * *